United States Patent [19]

Badwal

[11] Patent Number: 5,037,525
[45] Date of Patent: Aug. 6, 1991

[54] COMPOSITE ELECTRODES FOR USE IN SOLID ELECTROLYTE DEVICES

[75] Inventor: Sukhvinder P. S. Badwal, Mulgrave, Australia

[73] Assignee: Commonwealth Scientific and Industrial Research Organisation, Australia

[21] Appl. No.: 492,254

[22] Filed: Mar. 12, 1990

Related U.S. Application Data

[63] Continuation of Ser. No. 320,811, Mar. 9, 1989, abandoned, which is a continuation of Ser. No. 100,818, Aug. 20, 1987, abandoned.

[30] Foreign Application Priority Data

Oct. 29, 1985 [AU] Australia .................. 3161/85
Oct. 15, 1986 [AU] Australia ......... PCT/AU86/00305

[51] Int. Cl.$^5$ ............................................ G01N 27/26
[52] U.S. Cl. .................................. 204/421; 204/424; 204/252; 204/283; 204/427; 429/33; 429/41; 429/44; 429/45

[58] Field of Search ............... 204/282, 283, 291, 292, 204/293, 421, 424, 427, 252; 75/232, 234, 235; 429/40, 44, 45, 50, 33, 41; 427/74, 123, 125, 126.3, 126.5

[56] References Cited

U.S. PATENT DOCUMENTS 3,914,169 10/1975 Horowitz ..................... 204/195 S
4,421,579 12/1983 Covitch et al. ................. 204/279
4,545,886 10/1985 de Nora et al. ................. 204/252

Primary Examiner—John F. Niebling
Assistant Examiner—Kathryn Gorgos
Attorney, Agent, or Firm—Sughrue, Mion, Zinn, Macpeak & Seas

[57] ABSTRACT

A composite electrode material for use in solid electrolyte devices, which comprises a mixture of a noble metal and a semiconducting metal oxide with either electronic (n-type) or hole (p-type) conductivity.

15 Claims, 24 Drawing Sheets

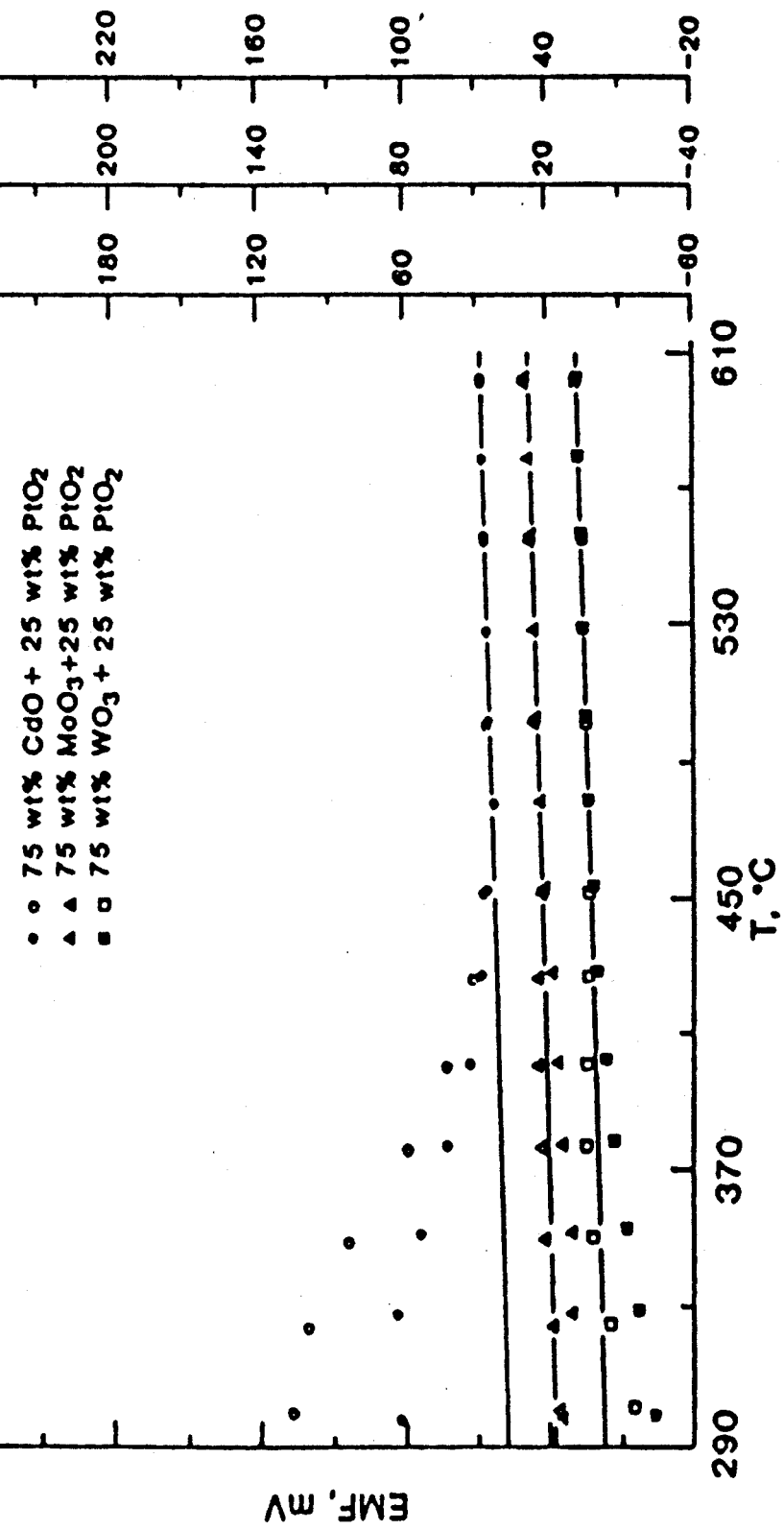

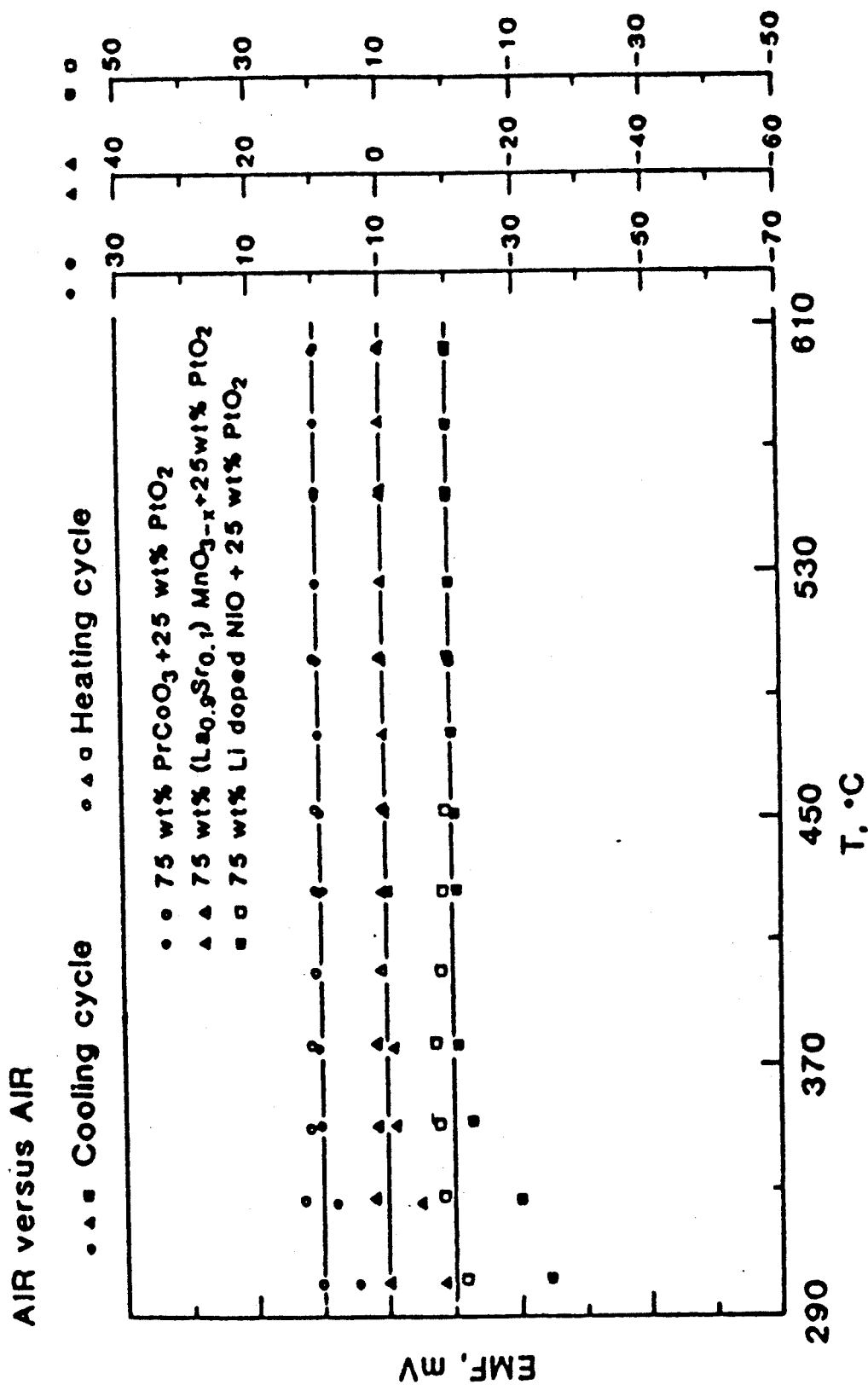

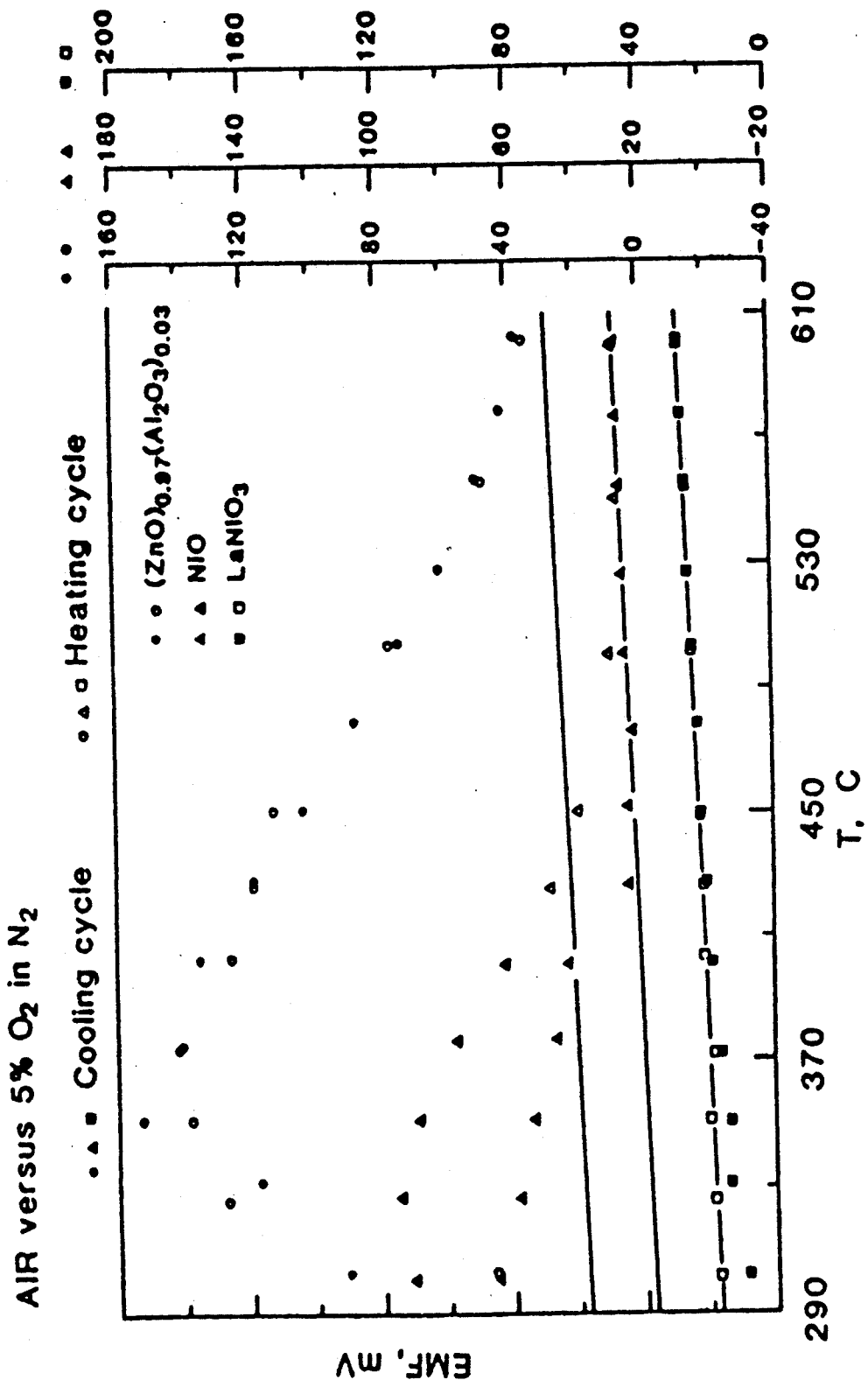

COMPOSITE ELECTRODES FOR USE IN SOLID ELECTROLYTE DEVICES

This is a continuation of application No. 07/320,811 filed Mar. 9, 1989 now abandoned, which in turn is a continuation of 07/100,818 filed Aug. 20, 1987, now abandoned.

This invention relates to composite electrodes which are intended for use in solid electrolyte devices. Such devices may include, for example, oxygen sensors, oxygen pumps, fuel cells, steam electrolysis cells, and electrochemical reactors.

BACKGROUND OF THE INVENTION

Solid electrolyte devices of interest usually consist of an oxygen ion conducting electrolyte membrane held between two electrodes. The examples of solid electrolyte materials include zirconia, both partially or fully stabilized by the addition of calcia, magnesia, yttria, scandia or one of a number of rare earth oxides, and thoria or ceria doped with calcia or yttria or a suitable rare earth oxide. The electrodes for these devices usually consist of porous coatings of metals such as Pt, Ag, Au, Pd, Ni and Co or metal oxides with good electronic conductivity. The electrodes participate in the charge transfer reaction between gaseous oxygen molecules or fuels (such as hydrogen, carbon monoxide or methane) and oxygen ions in the solid electrolyte by donating or accepting electrons. The electrode may also help to catalyze the reaction. For example Pt, the most commonly used electrode material on solid electrolyte oxygen sensors and oxygen pumps, shows high catalytic activity at temperatures above 600°-700° C. for the oxygen charge transfer reaction ($O_2 + 4e \rightleftharpoons 2O^{2-}$) at the electrode/electrolyte interface. The physical and chemical characteristics of the electrode play an important role in determining the speed of response and efficiency of the solid electrolyte devices.

The potentiometric or Nernst sensor consists of an oxygen ion conducting membrane of a solid electrolyte (with negligible electronic conductivity) such as fully or partially stabilized zirconia, and two electrodes reversible to $O_2/O^{2-}$ redox equilibria. If both electrodes of such a cell are exposed to different oxygen partial pressures, an emf is established across the cell which with respect to air, as the reference atmosphere is given by the nernst equation:

$$E(mV) = 0.0496 T \text{ Log } (0.21/pO_2)$$

where $pO_2$ is the unknown oxygen partial pressure and $T$ is the absolute temperature. The emf is measured by making electrical contacts to the electrodes.

Australian Patent No. 466,251 describes various geometrically distinct forms of a solid electrolyte oxygen sensor. The most commonly-used form is that of a tube, either open-ended or closed at one end, made entirely from the solid electrolyte. Other designs use the solid electrolyte as a disc or pellet, sealed in one end of a metal or ceramic supporting tube. In all cases, the reference environment, which is generally air, is maintained on one side of the tube (commonly on the inside) and the test environment is exposed to the other side of the tube.

In a potentiometric sensor, the current carrying capabilities of the electrodes are not important although electrodes with high charge transfer rates are required especially for low temperature (below 600° C.) applications of the sensors. The solid electrolyte oxygen sensors with noble metal electrodes are generally used above 600°-700° C. Below these temperatures they suffer from slow response rates, high impedance, susceptibility to electrical noise pick-up, large errors and exceptionally high sensitivity to impurities in the flue gases.

Other solid state electrochemical devices such as oxygen pumps, fuel cells, steam electrolyzers and electrochemical reactors may consist of a tube of fully or partially stabilized zirconia electrolyte with electrodes coated both on the outside and inside of the tube. A number of such cells may be connected in series and/or parallel to achieve the desired characteristics. For example, in an oxygen pump a number of cells may operate in conjunction to increase the yield of oxygen. In a fuel cell arrangement a number of the small cells may be connected in series and parallel to increase the total current and voltage output as maximum theoretical voltage achievable from a single cell is around 1.0-1.5 volts. In all these systems, the current carrying capacity and hence the overall efficiency of the cell is determined by (i) the electrode/electrolyte interfacial resistance to charge transfer reaction and (ii) the electrolyte resistance. The interfacial resistance to charge transfer depends mainly on the electrochemical behavior, and physical and chemical nature of the electrode. Because of the high electrode and electrolyte resistance at low temperature, the cells need to be operated at temperatures in the vicinity of 900°-1000° C. For optimum efficiency and increased cell life it is essential that these cells be operated at lower temperatures. The voltage losses across the electrolyte can be reduced by the use of thin and mechanically strong electrolyte films. Since conventional metal or metal oxide only electrodes have high electrode resistance at lower temperatures, it is necessary, therefore, to devise better electrode materials in order to reduce overpotential losses across the electrode/electrolyte interface.

SUMMARY OF THE INVENTION

We have found that semiconductor metal oxides with either electron (n-type) or hole (p-type) conduction when combined with noble metals such as Pt (referred to here-in-after as composite electrodes) are much better electrodes, than either metal or metal oxide only electrodes. These electrodes when used in oxygen sensors, lower their operating temperature to 300° C., well below the 600° C. achievable with conventional metal or metal oxide electrodes. In addition when these composite electrodes are used in other solid electrochemical devices, they increase their efficiency and enable them to be operated at temperatures lower than those achievable with conventional metal or metal oxide only electrodes. Moreover, these composite electrodes have superior physical characteristics such as resistance to grain growth and better adhesion to the electrolyte surface when compared with metal or metal oxide electrodes, respectively.

The improved electrochemical behavior is due to both constituents of the composite electrode participating in dissociation/diffusion/charge transfer reactions near and at the electrode/electrolyte interface.

One objective of the present invention, therefore, is to provide electrodes for solid electrolyte oxygen sensors which enable such sensors to generate ideal (i.e. Nernstian) emfs under oxygen-excess gaseous condition at temperatures substantially below those at which conventional noble metal or metal oxide electrodes begin to show non-ideal behavior. A further objective is to provide electrodes, which retain their good low temperature behavior after exposure to temperatures as high as 900° C.

In solid electrolyte devices such as oxygen pumps, fuel cells electrochemical reactors and steam electrolysis cells, the low electrode/electrolyte interfacial resistance to charge transfer reactions, and, consequently, the current carrying capabilities and current potential characteristics of the electrodes are of utmost importance as distinct from potentiometric oxygen sensors.

A further objective of the present invention is to provide electrode materials for oxygen pumps, fuel cells, electrochemical reactors and steam electrolysers to increase their efficiency, reduce energy losses and increase their useful life time by operation at lower temperatures.

According to the present invention, therefore, there is provided a composite electrode material for use in solid electrolyte devices, which comprises a mixture of a noble metal and a semiconducting metal oxide with either electronic (n-type) or hole (p-type) conductivity.

Preferably, the noble metal is platinum, silver, gold, iridium, rhodium or palladium or mixtures or alloys of any two or more of these metals.

The semiconductor metal oxide may be chosen from any suitable oxide which is a good electronic conductor and possesses other required attributes such as thermal stability and chemical compatibility with the solid electrolyte. Usually the oxide will be selected from semiconducting oxides of one or more of the Transition Metals, Lanthanides or Actinides. In this specification the "Transition Metals" are those having Atomic Nos. 21-30, 39-48 and 72-80.

For use in solid electrolyte devices, such as oxygen sensors, oxygen pumps, fuel cells, electrochemical reactors or steam electrolysis cells, the composite electrode material may be provided in the form of a surface layer on a solid electrolyte body.

According to one embodiment of the invention, the surface layer may consist of a thin porous coating of a mixture of the noble metal(s) and particles of the semiconducting oxide.

The invention also includes methods for producing the composite electrode materials of the invention.

The components of the electrode material may be applied to a solid electrolyte surface by any suitable known coating method, such as painting, sputtering, ion implantation, spraying or other in-situ chemical or electrochemical techniques. It is preferred to prepare the semiconducting oxide material before application, although it is possible (where appropriate) to apply precursors or individual components of the oxide material (or compounds which will produce them) in intimate admixture and to produce the semiconducting metal oxide by sintering the coating. The noble metal is applied with the oxide material (or its component oxides). Either the elemental metal or a suitable compound which can be heat-decomposed to the metal can be used.

The electrode materials of this invention permit the construction of solid state electrochemical cells with a low interfacial impedance between the electrode and the solid electrolyte. Similar devices with conventional noble metal or metal oxide only electrodes show a much higher electrode/electrolyte interfacial impedance.

The electrode materials of the present invention also permit the construction of oxygen sensors whose performance under typical air-excess combustion conditions conform to the Nernst equation down to temperatures as low as 300° C. The same sensor with conventional noble metal or metal oxide only electrodes depart significantly from the Nernst equation below 450° C. Sensors equipped with electrodes of the present invention may, therefore, be used to measure the oxygen potential of gases (e.g. boiler flue gases, internal combustion engine exhausts) in the temperature range 300° C.–700° C., where sensors with conventional electrodes require supplementary heating to generate Nernstian emfs. For gases below 300° C., the electrodes of the present invention enable sensors to operate with supplementary heating to bring them to a temperature in the range of 300° C.–400° C., whereas sensors with conventional electrodes are generally heated above 700° C. The lower operating temperature reduces the explosion hazard associated with maintaining heated sensors in the flue of a combustion device such as a boiler.

The invention also includes solid electrolyte devices which incorporate a solid electrode in accordance with the invention.

BRIEF DESCRIPTION OF THE DRAWINGS

In the following description, reference will be made to the accompanying drawings, in which:

In FIGS. 8 to 18, the solid lines represent the theoretical response and the symbols show the measured responses. In the interest of clarity, the vertical scales for FIGS. 8 to 18 have been offset for each set of data, as shown by the scale bars at the right of each figure.

Figure 1:
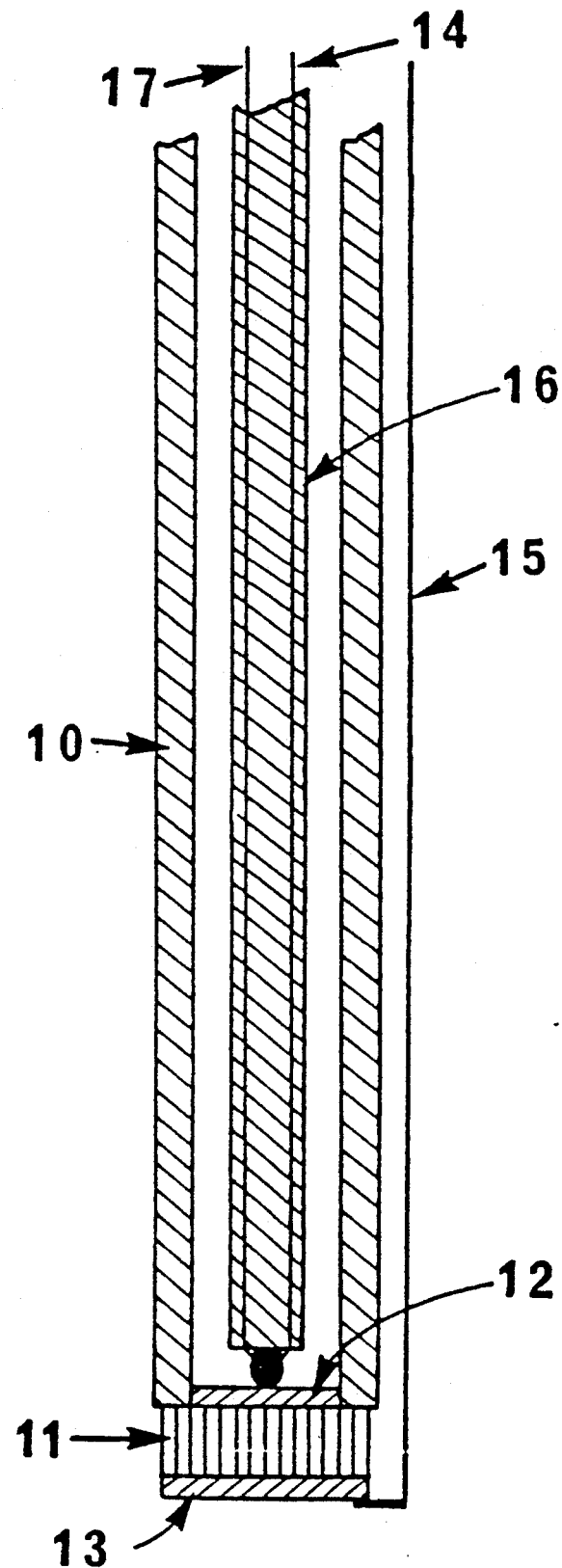
FIG. 1 shows a longitudinal section of an oxygen sensor embodying the electrodes of the invention.

One form of a complete sensor for use in gases, incorporating the electrode materials of the present invention, is shown in FIG. 1. A hollow ceramic body 10 is closed at one end by a solid electrolyte disc 11. Electrodes 12 and 13 of the present invention are located at the inner and outer surfaces, respectively, of disc 11. Electrical contact to the electrodes is made by metal wires 14 and 15. Wire 14 is pressed against electrode 12 by spring loading (not shown), applied by means of insulating tube 16. Tube 16 may also be used to convey a reference gas, e.g., air, to electrode 12. If tube 16 is a multi-bore tube, it may also carry a thermocouple (wires 14 and 17) to determine the temperature of electrolyte disc 11, in which case wire 14 form one leg of the thermocouple.

An alternative to wires 14 and 15 for electrical contact to the electrodes 12 and 13 is to use coatings, e.g., of platinum, gold, palladium, silver or their alloys, or of the electrode material itself, on the inside and outside surfaces of ceramic body 10, extending from electrodes 12 and 13 to the open end of the sensor. Such coatings may completely cover the surfaces of ceramic body 10, or they may consist of continuous strips covering only part of ceramic body 10.

For use in molten metals, outer electrode 13 is not required. Electrical contact must be made to the molten metal in the vicinity of the sensor, using an electrical conductor such as wire 15 attached to the sensor but not direct contact with solid electrolyte disc 11, or using a metallic coating on the outer surface or ceramic body 10 as hitherto described, or using a separate electrical conductor adjacent to the sensor. For measurements over extended periods, it is essential that the external electrical contact not dissolve in, or otherwise be attacked by, the molten metal. If a gaseous reference, e.g., air, is used the internal electrode 12 and electrical contact 14 are required.

For use in either gases or molten metals, a further alternative is for the solid electrolyte to take the form of a closed-end tube or other similar hollow shape, replacing both disc 11 and ceramic body 10. Another alternative, particularly appropriate when measuring gases, is for the reference environment, e.g. air, to contact external electrode 13 and for the gas or molten metal under test to occupy the inside of the sensor. In the case of a gas, it may be conveyed to internal electrode 12 by means of tube 16.

Figure 2:
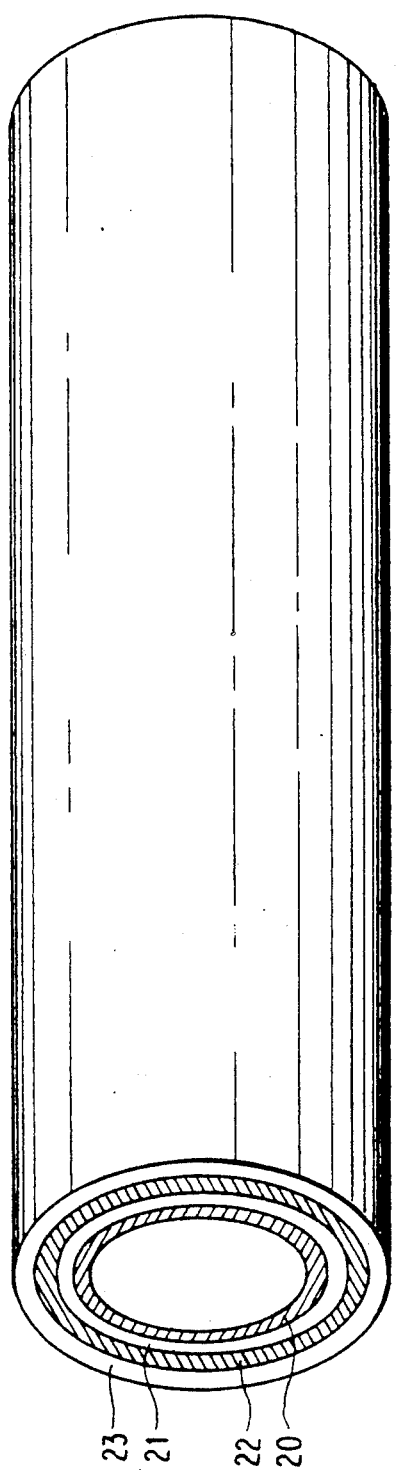
FIG. 2 shows one form of a cell for use in solid electrochemical devices such as oxygen pumps, fuel cells, electrochemical reactors or steam electrolysers.

One form of a cell to be used in solid electrochemical devices other than oxygen sensors is shown in FIG. 2. A hollow porous ceramic substrate body 20 is coated with a thin layer 21 of the electrodes of the present invention. The impervious electrolyte layer 22 is then formed on this electrode by a suitable combination of ceramic processing techniques. The outer electrode layer 23 of the materials of the present invention is then formed on the outer surface of the electrolyte layer. An alternative to this arrangement is not to use a porous substrate support but to coat electrodes of the present invention both on the inside and outside of a presintered electrolyte tube.

The following examples illustrate the preparation of the composite electrodes of this invention and the behavior of solid electrolyte cells incorporating such electrodes.

EXAMPLE 1

In order to show the superior characteristics of composite electrodes of the present invention over individual metal or metal oxides, the materials were selected from a wide spectrum of semiconducting oxides. These included: (i) different crystal structure, (fluorite, rutile, orthorhombic, hexagonal, monoclinic etc.); (ii) varying degree of nonstoichiometry (e.g. $V_2O_5$, $LaNiO_3$ and $Cr_2O_3$ versus $PrO_{2-y}$, $TbO_{2-y}$, $(Pr_z Gd_{1-z})O_{2-x}$, $(Nd_{0.9} Sr_{0.1})CoO_{3-x}$ etc.); (iii) simple transition metal oxides ($CoO$, $NiO$, $MnO_2$, $ZnO$ etc.); (iv) rare earth oxides ($CeO_{2-x}$, $PrO_{2-y}$, $TbO_{2-y}$); (v) compounds between two and three metal oxides ($CrVO_4$, $CrNbO_4$, $LaCrO_3$, $PrCoO_3$, $(La_{0.8} Sr_{0.2}) CrO_{3-x}$, $(Nd_{0.9} Sr_{0.1})CoO_{3-x}$ etc.); (vi) solid solutions $[(U_z M_{1-z})O_{2\pm x}(M=Sc, Y, Pr, Dy), (Pr_z Gd_{1-z})O_{2-x}]$; and (vii) materials with n-type (electron conduction) or p-type (hole conduction) conductivity.

The simple transition metal and rare earth oxides were obtained from chemical manufacturing companies. Solid solutions and compounds between two or more metal oxides were prepared by one of the following methods:

(i) Metal salts to give required composition were dissolved in aqueous media followed by coprecipitation with aqueous ammonia solution. The coprecipitated powder was dried and calcined at high temperatures to complete the reaction.

(ii) The second method involved dissolving the metal nitrates (in the desired quantity) in water and carefully drying the solution. This was followed by grinding the dried material and firing at high temperatures.

(iii) The transition metal oxides were mixed thoroughly in ethanol, dried and heated at high temperatures. In many cases, it was necessary to grind and refire the powder several times to complete the reaction.

The completion of the reaction between metal oxides was detected by taking X-ray diffractograms of the fired powders and comparing the results with the literature data.

Various metal oxides tested are listed in Table 1.

TABLE 1

Composition, nomenclature and crystal structure of various semiconductor metal oxides tested.

| No. | Nomenclature | Composition of metal oxide | Crystal structure |
|---|---|---|---|
| 1 | A1 | $PrO_{2-y}$ | |
| 2 | A2 | $TbO_{2-y}$ | |
| 3 | A3 | $CeO_{2-x}$ | |
| 4 | A4 | $Cr_2O_3$ | |
| 5 | A5 | $NiO$ | |
| 6 | A6 | $CoO$ | |
| 7 | A7 | $Fe_2O_3 + Fe_3O_4$ | |
| 8 | A8 | $ZnO$ | |
| 9 | A9 | $MnO_2$ | |
| 10 | A10 | $SnO_2$ | |
| 11 | A11 | $WO_3$ | |
| 12 | A12 | $MoO_3$ | |
| 13 | A13 | $CdO$ | |
| 14 | A14 | $V_2O_5$ | |
| 15 | A15 | $In_2O_3$ | |
| 16 | A16 | $CrVO_4$ | |
| 17 | A17 | $CrNbO_4$ | |
| 18 | A18 | $CrUO_4$ | |
| 19 | A19 | $(ZnO)_{0.97} (Al_2O_3)_{0.03}$ | |
| 20 | A20 | $(ZnO)_{0.94} (ZrO_2)_{0.05}$ | |
| 21 | A21 | Li doped $NiO$ | |
| 22 | A22 | Sn doped $In_2O_3$ | |
| 23 | A23 | $NdCoO_3$ | |
| 24 | A24 | $LaCrO_3$ | |
| 25 | A25 | $LaMnO_3$ | |
| 26 | A26 | $LaNiO_3$ | |
| 27 | A27 | $LaCoO_3$ | |
| 28 | A28 | $PrCoO_3$ | |
| 29 | A29 | $La_2NiO_4$ | |
| 30 | A30 | $(NiO)_{0.5} (La_2NiO_4)_{0.5}$ | |

TABLE 1-continued

Composition, nomenclature and crystal structure of various semiconductor metal oxides tested.

| No. | Nomenclature | Composition of metal oxide | Crystal structure |
|---|---|---|---|
| 31 | A31 | $(La_{0.8}Sr_{0.2})CrO_{3-x}$ | |
| 32 | A32 | $(La_{0.9}Sr_{0.1})MnO_{3-x}$ | |
| 33 | A33 | $(Nd_{0.9}Sr_{0.1})CoO_{3-x}$ | |
| 34 | A34 | $(U_{0.4}Dy_{0.6})O_{2\pm x}$ | |
| 35 | A35 | $(Pr_zGd_{1-z})O_{2-x}$ | |

The subscripts "x" indicate a small departure and "y" indicate a large departure from the ideal oxygen/metal atom ratio for the oxide in question.

EXAMPLE 2

Fine pastes of various oxides listed in Table 1 in triethylene glycol were prepared by grinding the powdered oxide with a 25 percent solution of triethylene glycol in ethanol until the ethanol had evaporated. The procedure was repeated several times until a uniform and consistent paste was obtained.

EXAMPLE 3

A number of pastes of platinum dioxide and $(U_{0.38}Sc_{0.62})O_{2\pm x}$ in varying ratios were prepared by the procedure described in example 2. Table 2 gives the composite electrode compositions and nomenclature.

TABLE 2

Composition and Nomenclature of Composite Electrodes Described in Example 3

| Nomenclature | Electrode composition |
|---|---|
| US1 | 0 wt % $PtO_2$ + 100 wt % $(U_{0.38}Sc_{0.62})O_{2\pm x}$ |
| US2 | 15 wt % $PtO_2$ + 85 wt % $(U_{0.38}Sc_{0.62})O_{2\pm x}$ |
| US3 | 25 wt % $PtO_2$ + 75 wt % $(U_{0.38}Sc_{0.62})O_{2\pm x}$ |
| US4 | 35 wt % $PtO_2$ + 65 wt % $(U_{0.38}Sc_{0.62})O_{2\pm x}$ |
| US5 | 50 wt % $PtO_2$ + 50 wt % $(U_{0.38}Sc_{0.62})O_{2\pm x}$ |
| US6 | 75 wt % $PtO_2$ + 25 wt % $(U_{0.38}Sc_{0.62})O_{2\pm x}$ |
| US7 | 100 wt % $PtO_2$ + 0 wt % $(U_{0.38}Sc_{0.62})O_{2\pm x}$ |

EXAMPLE 4

A number of pastes of platinum dioxide and $CrNbO_4$ in varying ratios were prepared by the procedure described in example 2. Table 3 gives the composite electrode composition and nomenclature.

TABLE 3

Composition and Nomenclature of Electrodes Described in Example 4.

| Nomenclature | Electrode composition |
|---|---|
| CN1 | 0 wt % $PtO_2$ + 100 wt % $CrNbO_4$ |
| CN2 | 10 wt % $PtO_2$ + 90 wt % $CrNbO_4$ |
| CN3# | 25 wt % $PtO_2$ + 75 wt % $CrNbO_4$ |
| CN4 | 50 wt % $PtO_2$ + 50 wt % $CrNbO_4$ |
| CN5 | 75 wt % $PtO_2$ + 25 wt % $CrNbO_4$ |
| CN6* | 100 wt % $PtO_2$ + 0 wt % $CrNbO_4$ |

\# Same as B17 in Table 4
\*Same as US7 in Table 2

EXAMPLE 5

Fine pastes of composite electrodes comprising a mixture in triethylene glycol of 25 weight percent platinum dioxide and 75 weight percent of the metal oxide were prepared by the procedure described in example 2. The compositions of the composite electrodes are given in Table 4.

TABLE 4

Composition and nomenclature of composite electrodes.

Composite electrode

| Number | Nomenclature | composition |
|---|---|---|
| 1 | B1 | 25 wt % $PtO_2$ + 75 wt % $PrO_{2-y}$ |
| 2 | B2 | 25 wt % $PtO_2$ + 75 wt % $TbO_{2-y}$ |
| 3 | B3 | 25 wt % $PtO_2$ + 75 wt % $CeO_{2-x}$ |
| 4 | B4 | 25 wt % $PtO_2$ + 75 wt % $Cr_2O_3$ |
| 5 | B5 | 25 wt % $PtO_2$ + 75 wt % NiO |
| 6 | B6 | 25 wt % $PtO_2$ + 75 wt % CoO |
| 7 | B7 | 25 wt % $PtO_2$ + 75 wt % ($Fe_2O_3$ + $Fe_3O_4$) |
| 8 | B8 | 25 wt % $PtO_2$ + 75 wt % ZnO |
| 9 | B9 | 25 wt % $PtO_2$ + 75 wt % $MnO_2$ |
| 10 | B10 | 25 wt % $PtO_2$ + 75 wt % $SnO_2$ |
| 11 | B11 | 25 wt % $PtO_2$ + 75 wt % $WO_3$ |
| 12 | B12 | 25 wt % $PtO_2$ + 75 wt % $MoO_3$ |
| 13 | B13 | 25 wt % $PtO_2$ + 75 wt % CdO |
| 14 | B14 | 25 wt % $PtO_2$ + 75 wt % $V_2O_5$ |
| 15 | B15 | 25 wt % $PtO_2$ + 75 wt % $In_2O_3$ |
| 16 | B16 | 25 wt % $PtO_2$ + 75 wt % $CrVO_4$ |
| 17 | B17 | 25 wt % $PtO_2$ + 75 wt % $CrNbO_4$ |
| 18 | B18 | 25 wt % $PtO_2$ + 75 wt % $CrUO_4$ |
| 19 | B19 | 25 wt % $PtO_2$ + 75 wt % $[(ZnO)_{0.97}(Al_2O_3)_{0.03}]$ |
| 20 | B20 | 25 wt % $PtO_2$ + 75 wt % $[(ZnO)_{0.95}(ZrO_2)_{0.05}]$ |
| 21 | B21 | 25 wt % $PtO_2$ + 75 wt % (Li doped NiO) |
| 22 | B22 | 25 wt % $PtO_2$ + 75 wt % (Sn doped $In_2O_3$) |
| 23 | B23 | 25 wt % $PtO_2$ + 75 wt % $(NdCoO_3)$ |
| 24 | B24 | 25 wt % $PtO_2$ + 75 wt % $LaCrO_3$ |
| 25 | B25 | 25 wt % $PtO_2$ + 75 wt % $LaMnO_3$ |
| 26 | B26 | 25 wt % $PtO_2$ + 75 wt % $LaNiO_3$ |
| 27 | B27 | 25 wt % $PtO_2$ + 75 wt % $LaCoO_3$ |
| 28 | B28 | 25 wt % $PtO_2$ + 75 wt % $PrCoO_3$ |
| 29 | B29 | 25 wt % $PtO_2$ + 75 wt % $La_2NiO_4$ |
| 30 | B30 | 25 wt % $PtO_2$ + 75 wt % $[(NiO)_{0.5}(La_2NiO_4)_{0.5}]$ |
| 31 | B31 | 25 wt % $PtO_2$ + 75 wt % $[(La_{0.8}Sr_{0.2})CrO_{3-x}]$ |
| 32 | B32 | 25 wt % $PtO_2$ + 75 wt % $[(La_{0.9}Sr_{0.1})MnO_{3-x}]$ |
| 33 | B33 | 25 wt % $PtO_2$ + 75 wt % $[(Nd_{0.9}Sr_{0.1})CoO_{3-x}]$ |
| 34 | B34 | 25 wt % $PtO_2$ + 75 wt % $[(U_{0.4}Dy_{0.6})O_{2\pm x}]$ |
| 35 | B35 | 25 wt % $PtO_2$ + 75 wt % $[(Pr_zGd_{1-z})O_{2-x}]$ |

EXAMPLE 6

Several composite electrodes from Tables 2-4 were heated at 600° C. for 10-15 hours in air. The X-ray diffractograms of the heated electrodes showed that the platinum dioxide had decomposed to platinum without reacting with the metal oxide. In all the tests performed on composite electrodes to determine their electrode behavior they were given preheat treatment at 600° C. to decompose platinum dioxide to platinum. Although in all the tests, the composite electrodes consisted of platinum and the metal oxide but for convenience they will be referred to as consisting of the metal oxide and platinum dioxide (Tables 2-4). The final weight ratio of Pt/metal oxide differs only slightly from that $PtO_2$/metal oxide.

EXAMPLE 7A

The composite electrodes described in example 3 (Table 2) were painted on both flat faces of sintered discs of 7 mol % $Y_2O_3$ + 93 mol % $ZrO_2$ (YSZ7) electrolyte (diameter 9.6-9.7 mm, thickness ~2.5 mm and density ~95% of theoretical for the electrolyte discs) and heated to 600° C. for 15 hours in air. The USN/YSZ7/USN (N=1, 2, 3, 4, 5, 6 or 7) cells were then subjected to complex impedance measurements over the temperature and frequency ranges of 450°-600° C. and 0.5 mHz-1 MHz, respectively. Impedance measurements were made with a solartron 1174 frequency response analyzer. The electrode resistance, (which determines the rate of the oxygen exchange reaction at the electrode/electrolyte interface) and the time constant, $\tau_O$ which determines the speed of response of the solid electrochemical cells to perturbations such as change in the oxygen partial pressure were determined by the standard analysis of the impedance data in the complex plane.

Figure 3:
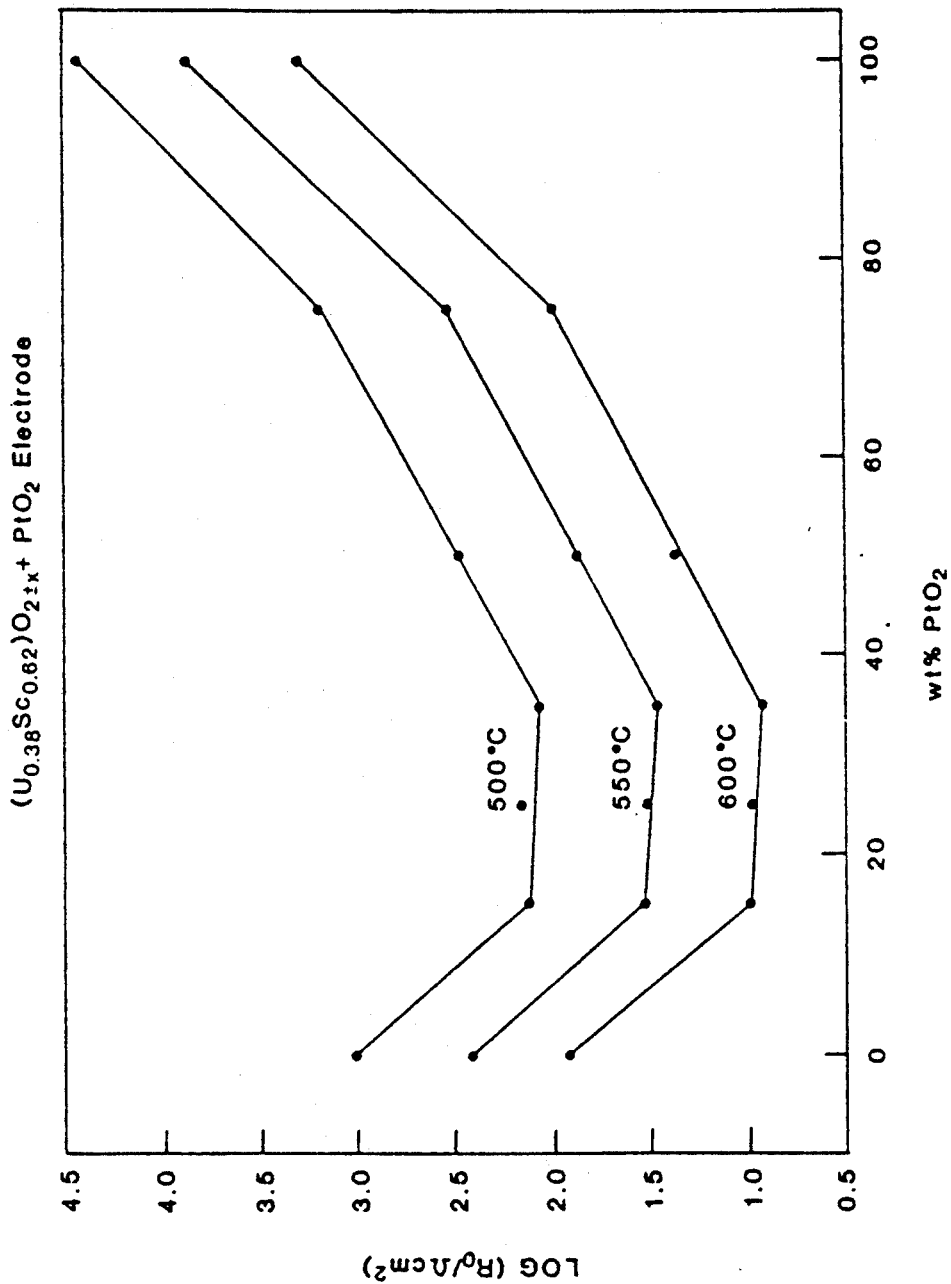
FIG. 3 is a graph showing plots of the electrodes resistance ($R_O$) versus composite electrode [consisting of $(U_{0.38} Sc_{0.62})O_{2+x}$ and $PtO_2$] composition at three different temperatures.

In FIG. 3, the electrode resistance, $R_o$ has been plotted against weight percent of platinum dioxide at several temperatures. The graphs show a minimum between 15 and 35 wt % $PtO_2$. The initial decrease of about an order of magnitude in the electrode resistance, on addition of a mere 15 wt % $PtO_2$ is dramatic. For $PtO_2$ content above 35 wt %, the electrode resistance increased very rapidly.

Figure 4:
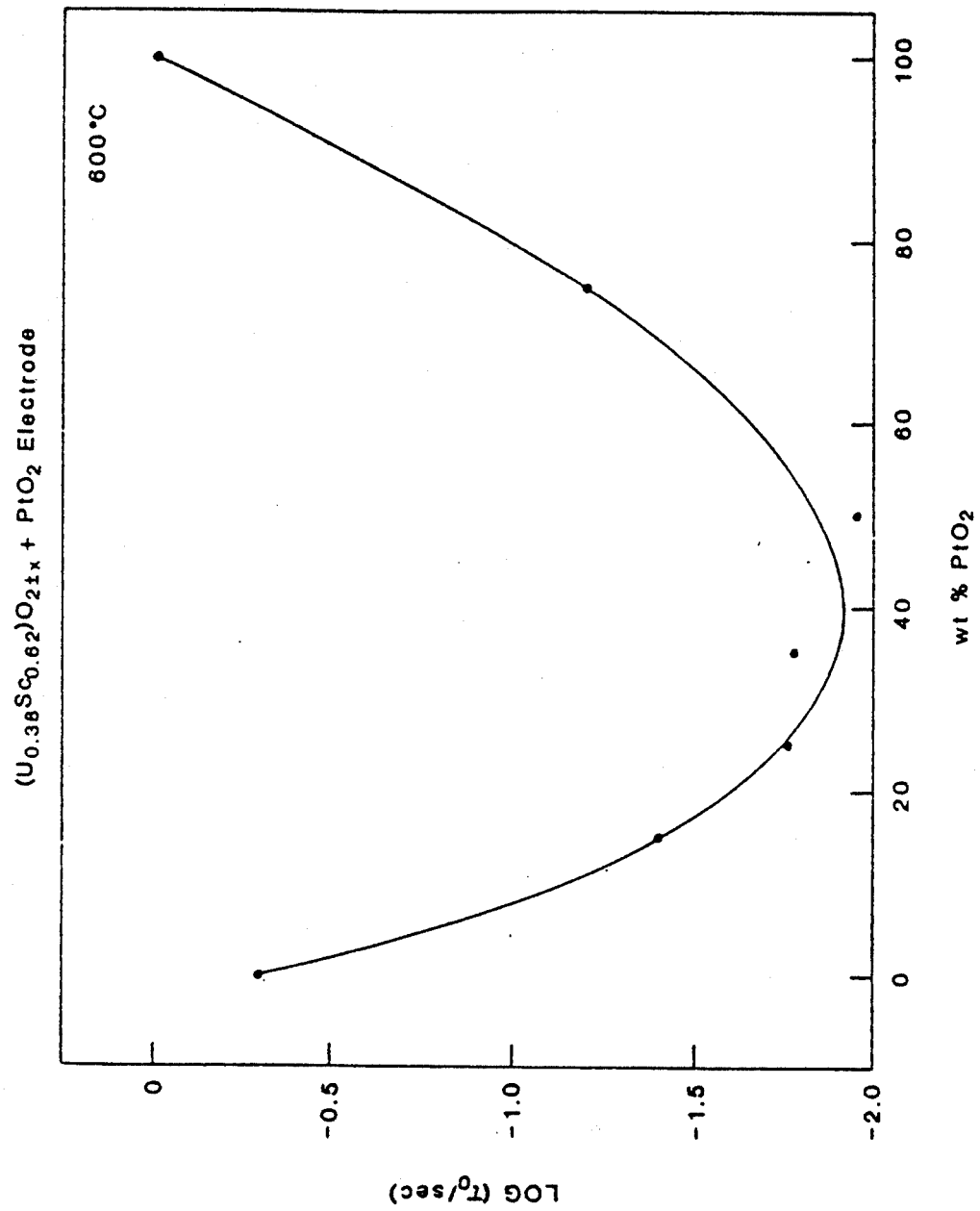
FIG. 4 is a graph showing a plot of the electrode time constant, $T_o$ versus composite electrode [consisting of $(U_{0.38} Sc_{0.62})O_{2+x}$ and $PtO_2$] composition at 600° C.

In FIG. 4, log $\tau_o$ is plotted against weight percent of platinum dioxide at 600° C. Again, this graph shows a minimum around 40 wt % $PtO_2$.

EXAMPLE 7B

Figure 5:
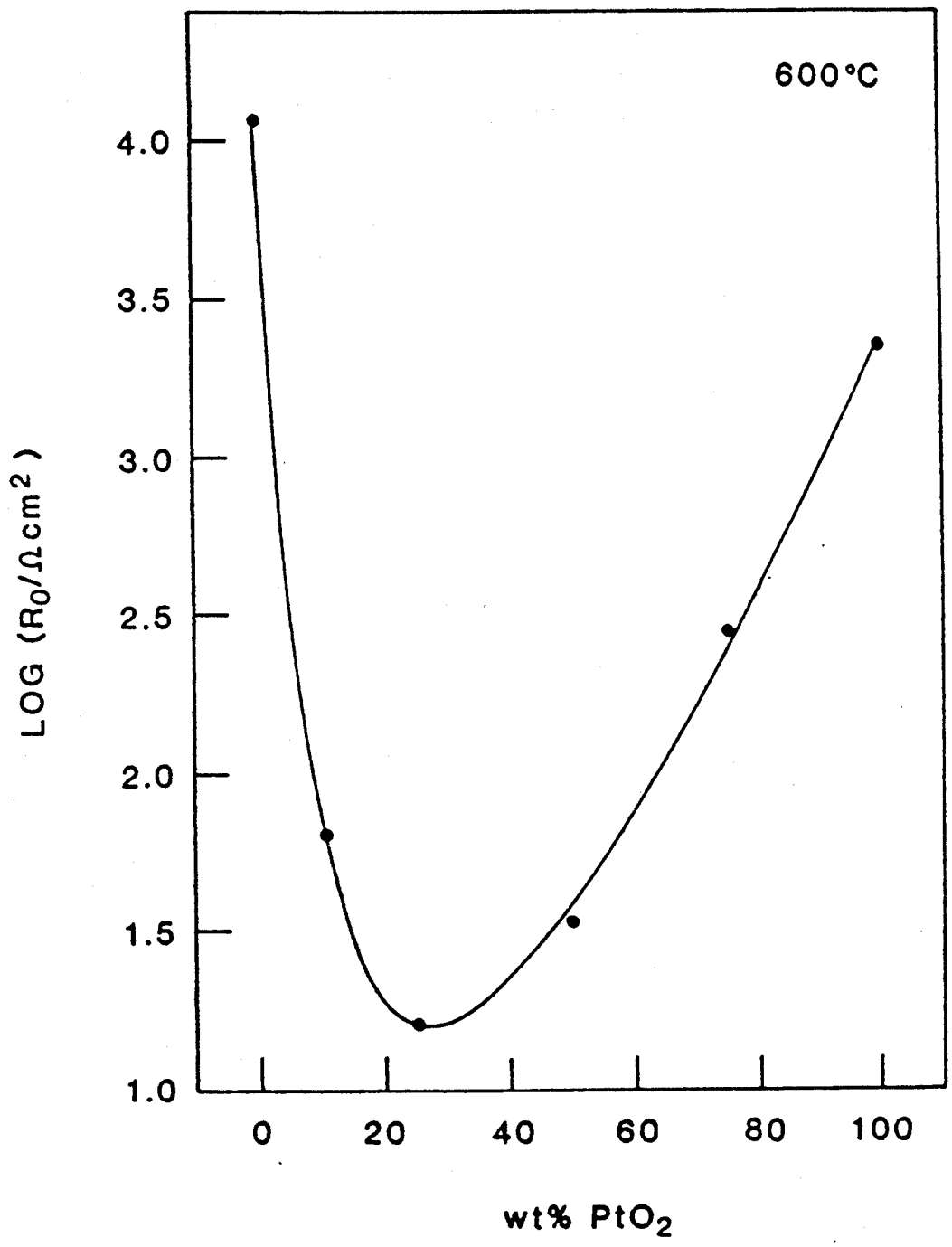
FIG. 5 is a graph showing a plot of the electrode resistance ($R_o$) versus composite electrode [consisting of $CrNbO_4$ and $PtO_2$] composition.
Figure 6:
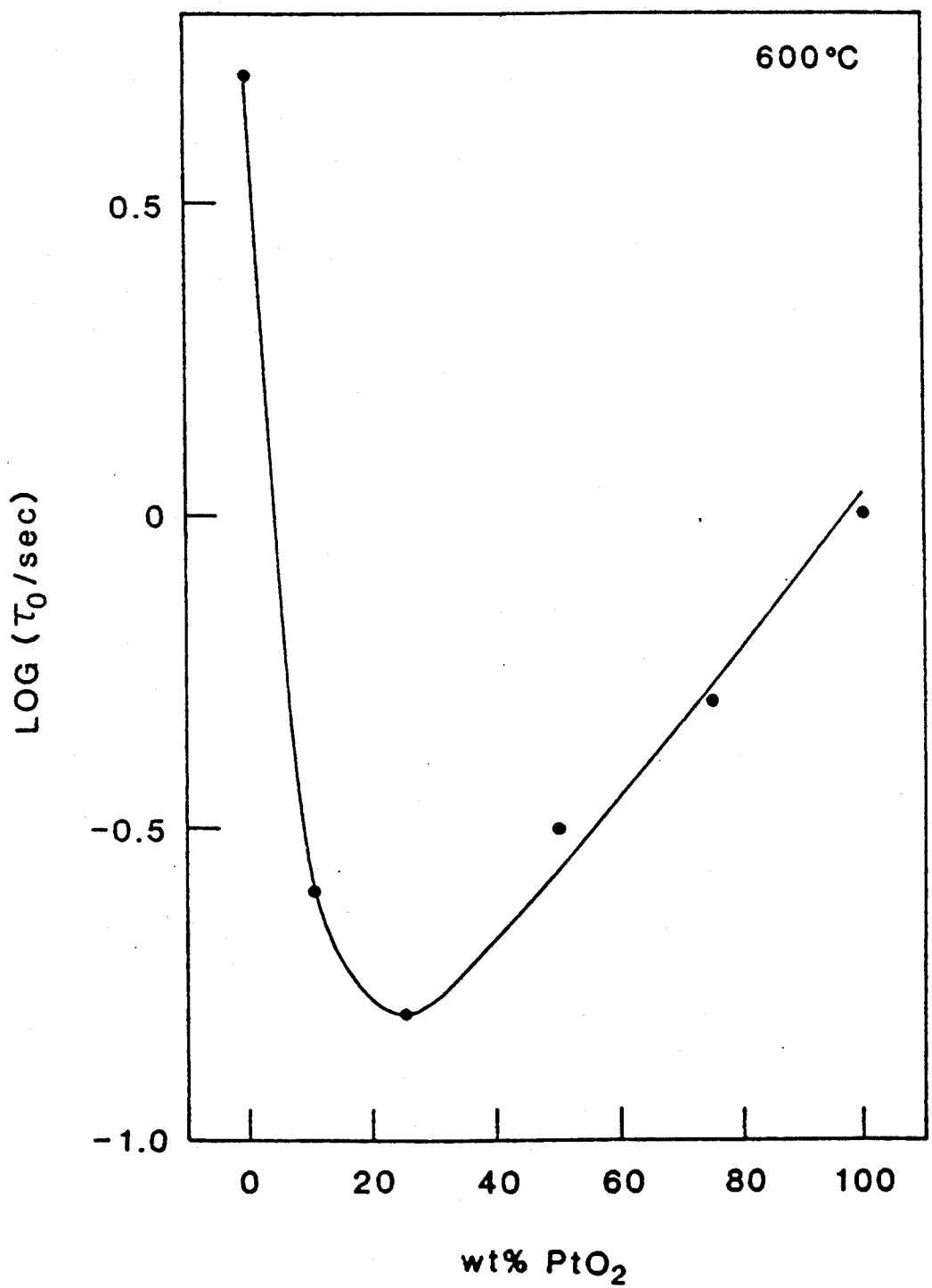
FIG. 6 is a graph showing a plot of the electrode time constant, $T_o$ versus composite electrode [consisting of $CrNbO_4$ and $PtO_2$] composition.

The composite electrodes described in example 4 (Table 3) were painted on 10 mol % yttria + 90 mol % zirconia electrolyte discs and subjectd to impedance measurements as per example 7A. FIG. 5 shows a plot of the electrode resistance and FIG. 6 a plot of the time constant versus weight percent of platinum dioxide for CNX/YSZ7/CNX (X=1, 2, 3, 4, 5 or 6) cells at 600° C. These graphs show a minimum in the the electrode resistance and the time constant around 25 wt % $PtO_2$.

The time constant and the electrode resistance of composite electrodes containing 25-40 wt % $PtO_2$ are at least an order of magnitude lower than those for either constituents of the composite. These results quite clearly show that the oxygen exchange reaction at the composite-electrode/electrolyte interface is much faster than at either metal/electrolyte or metal oxide/electrolyte interface. The results also show that both constituent of the composite electrode participate in the oxygen transfer kinetics.

Such phenomena observed for the materials of the present invention are unique and have not been observed or reported before.

EXAMPLE 8

Figure 7:
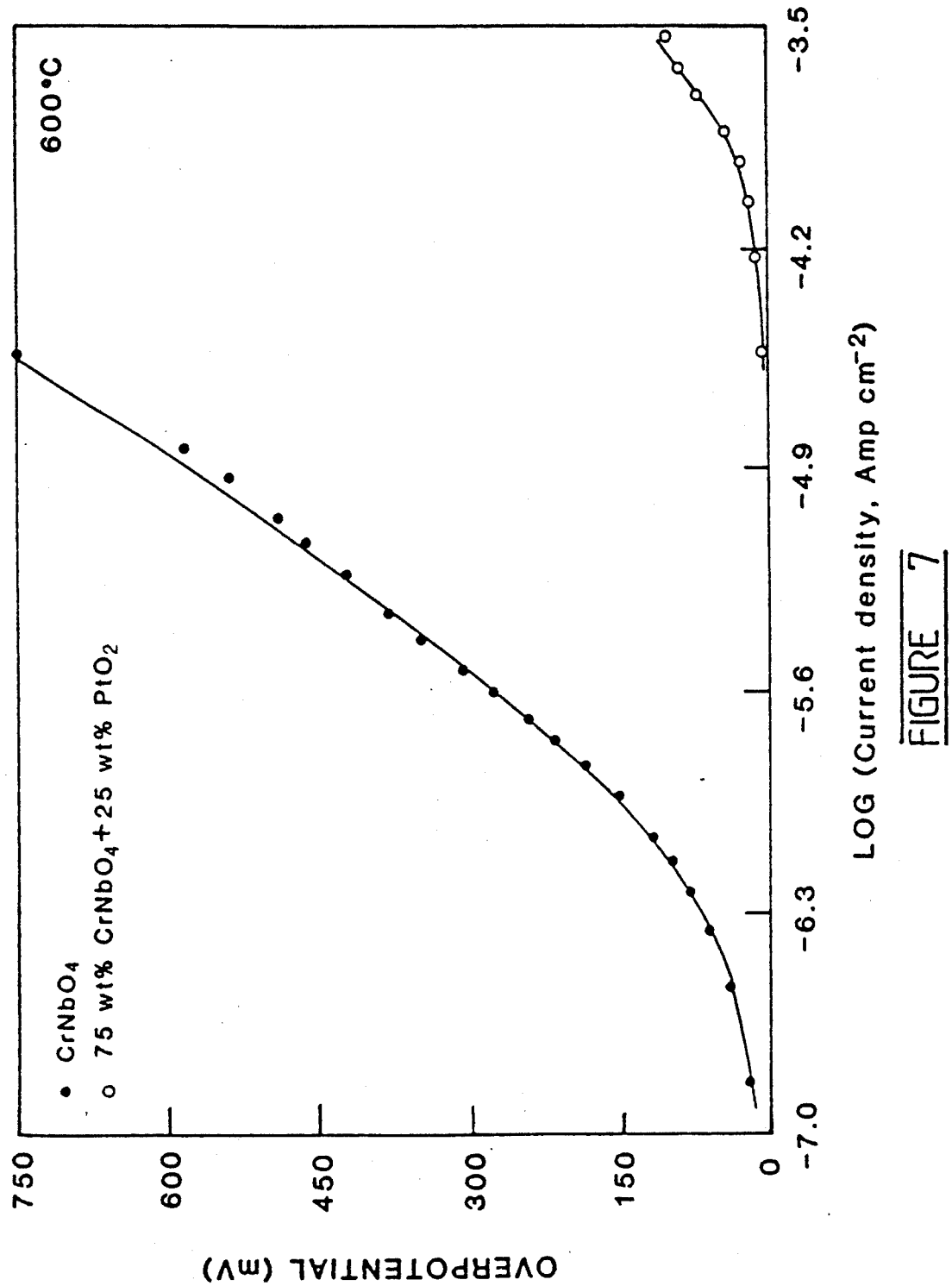
FIG. 7 is a graph comparing current voltage characteristics of a metal oxide ($CrNbO_4$) electrode with the composite electrode constituting 75 wt% of this metal oxide +25 wt% $PtO_2$.
Figure 8:
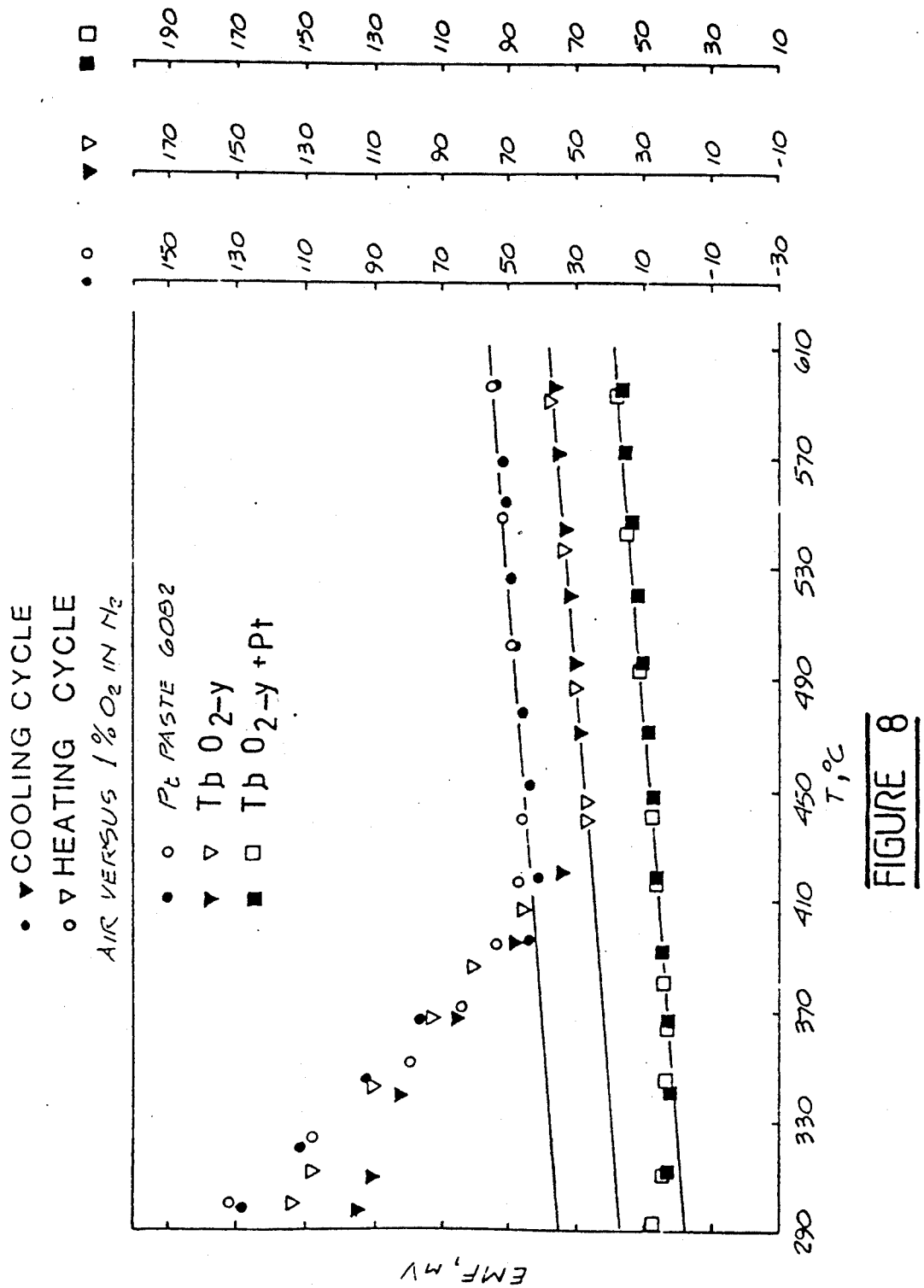
FIG. 8 is a graph showing the performance of oxygen sensors provided with one composite electrode material of the present invention including comparative results for sensors provided with either individual metal oxide or metal constituting the composite electrode.
Figure 9:
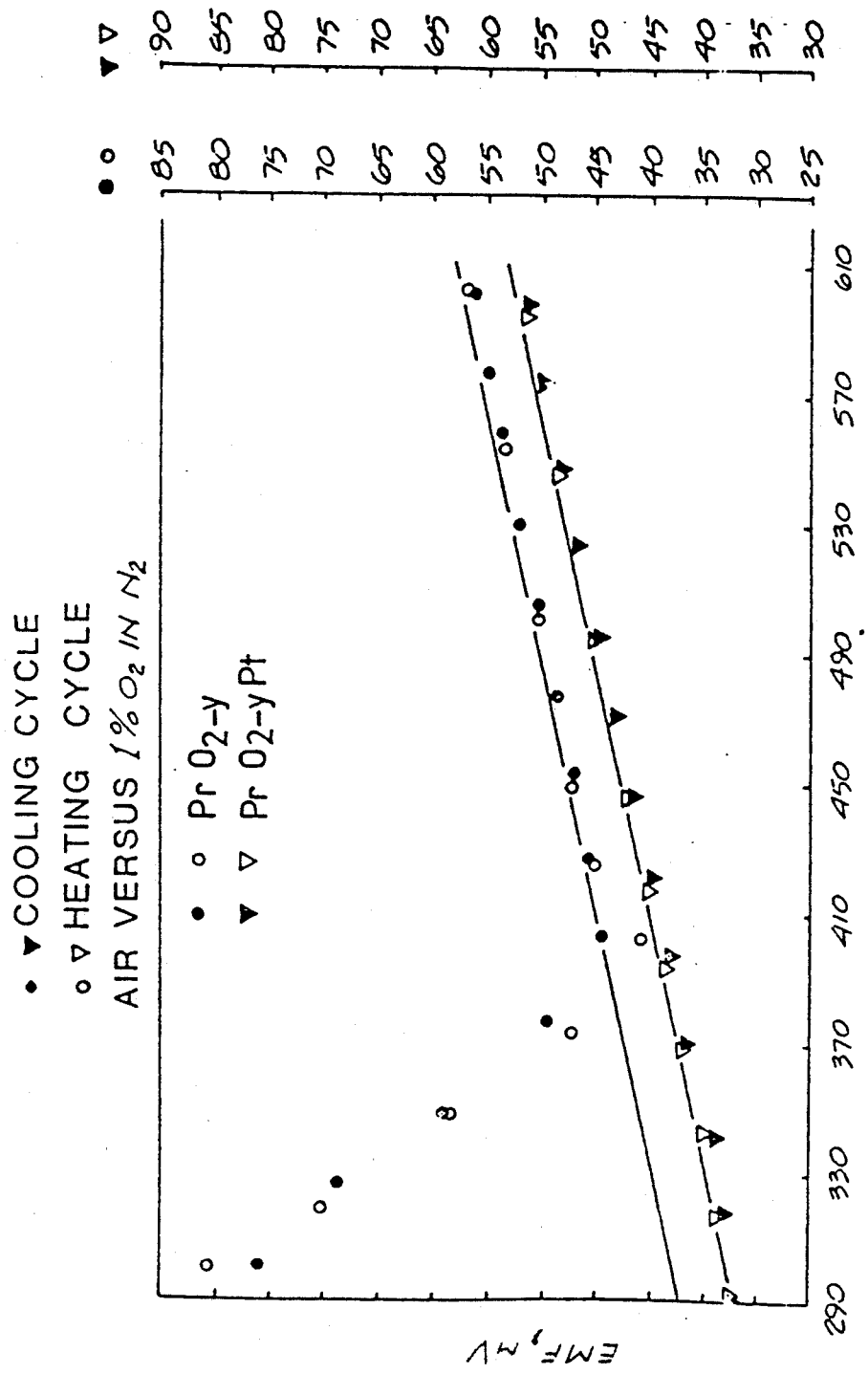
FIGS. 9-17 are graphs comparaing the sensor performance of various semiconducting metal oxides with the composite electrodes-constituting that metal oxide and Pt (added as $PtO_2$)
Figure 10:
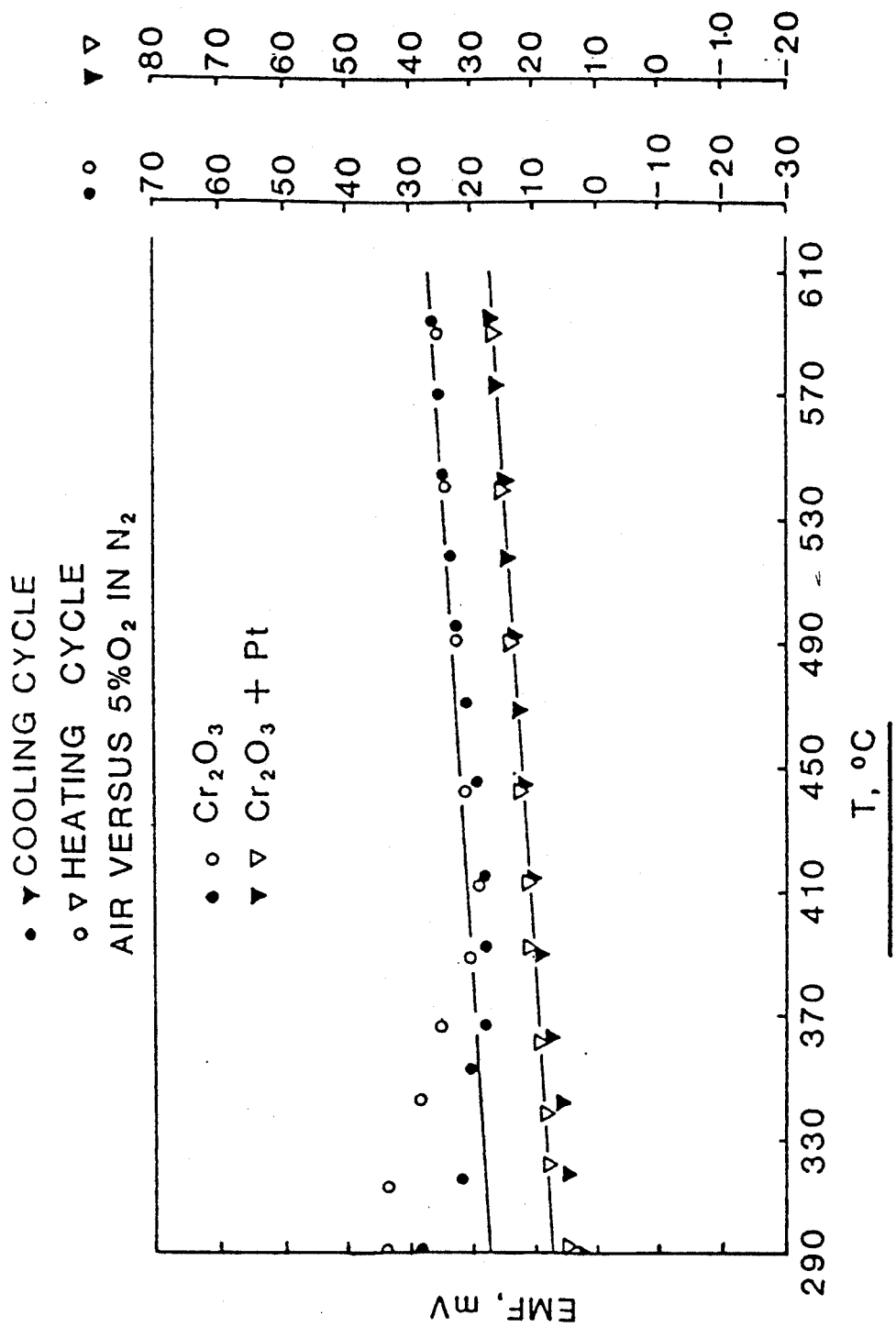
Figure 11:
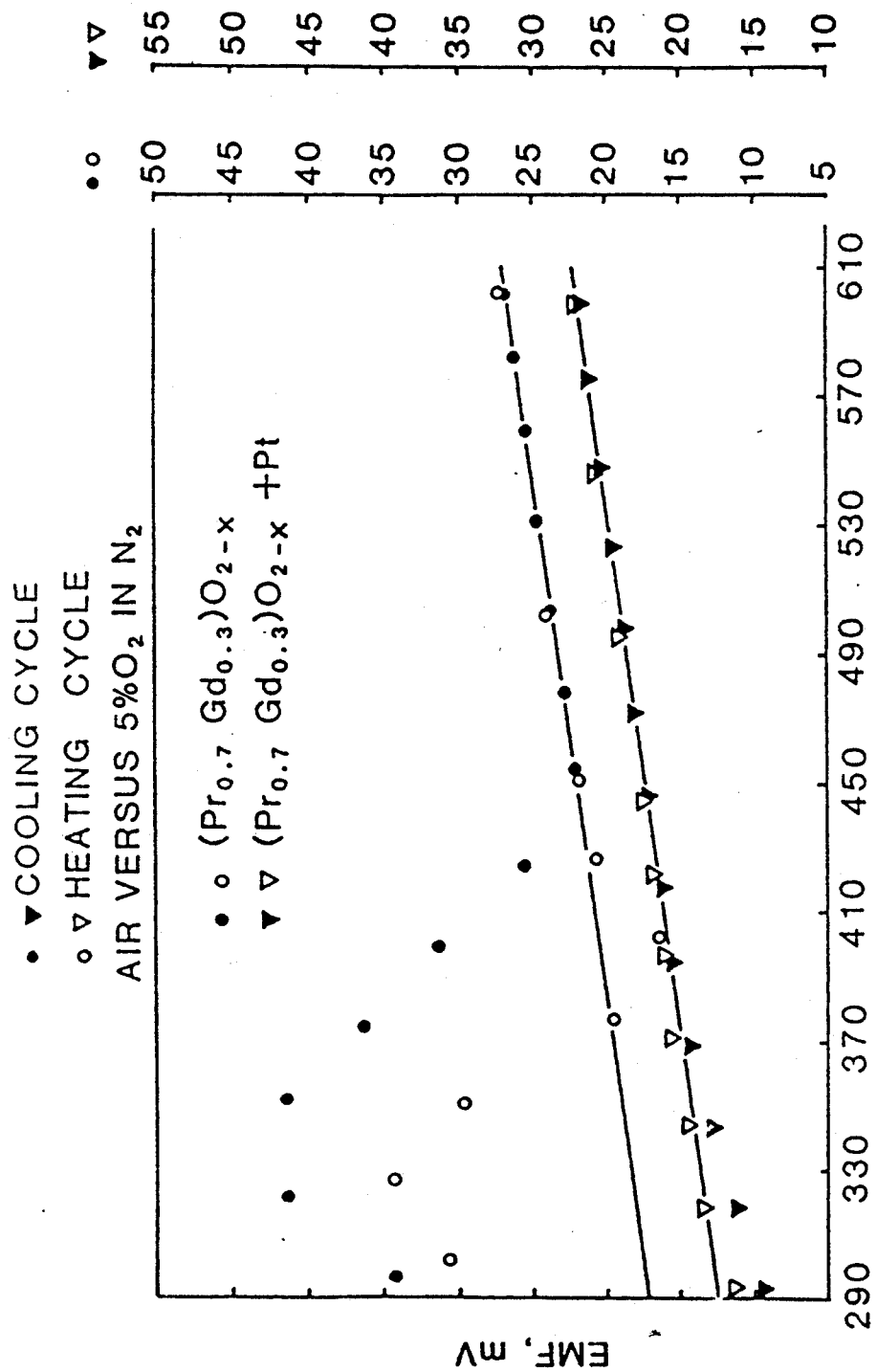
Figure 12A:
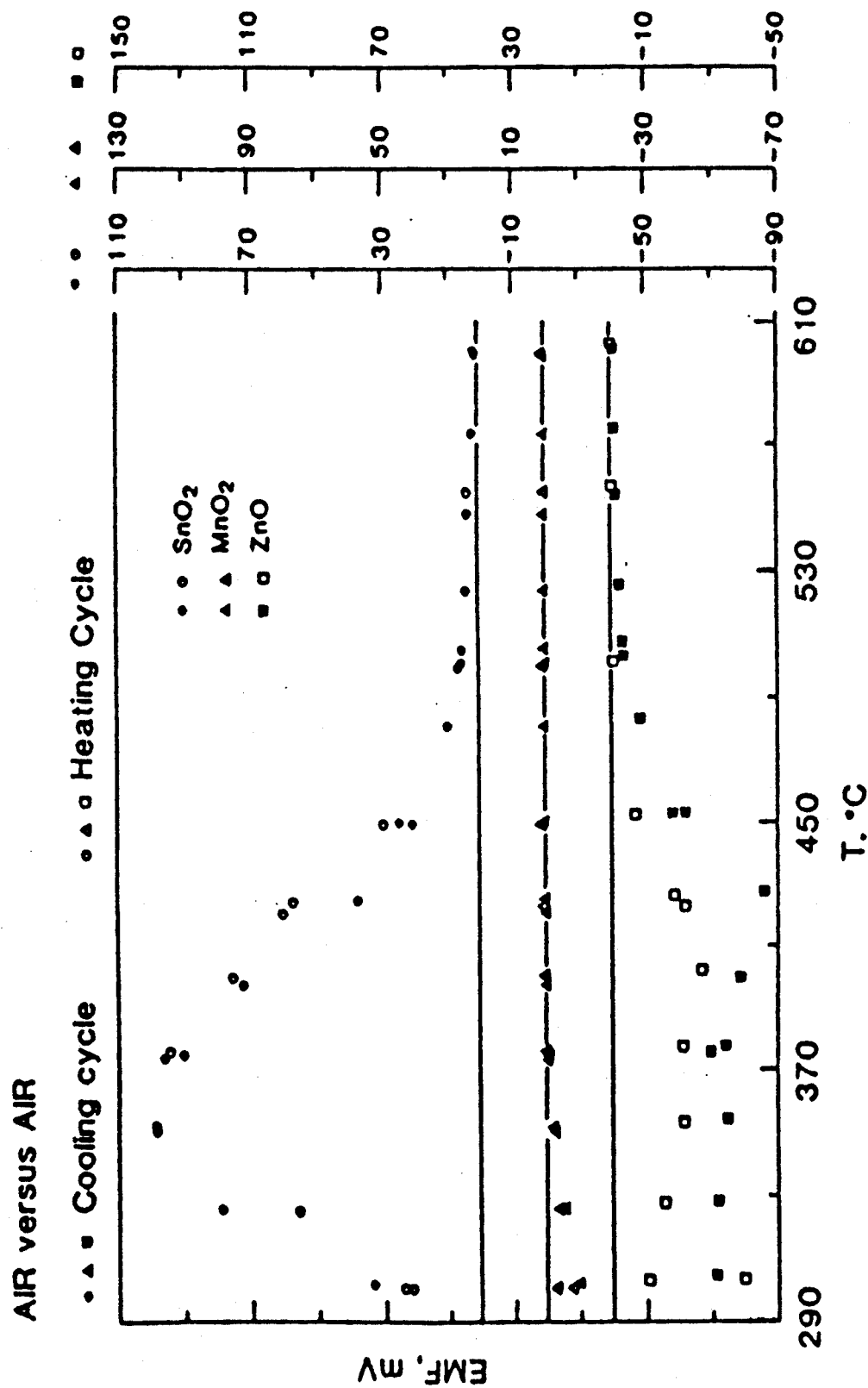
Figure 12B:
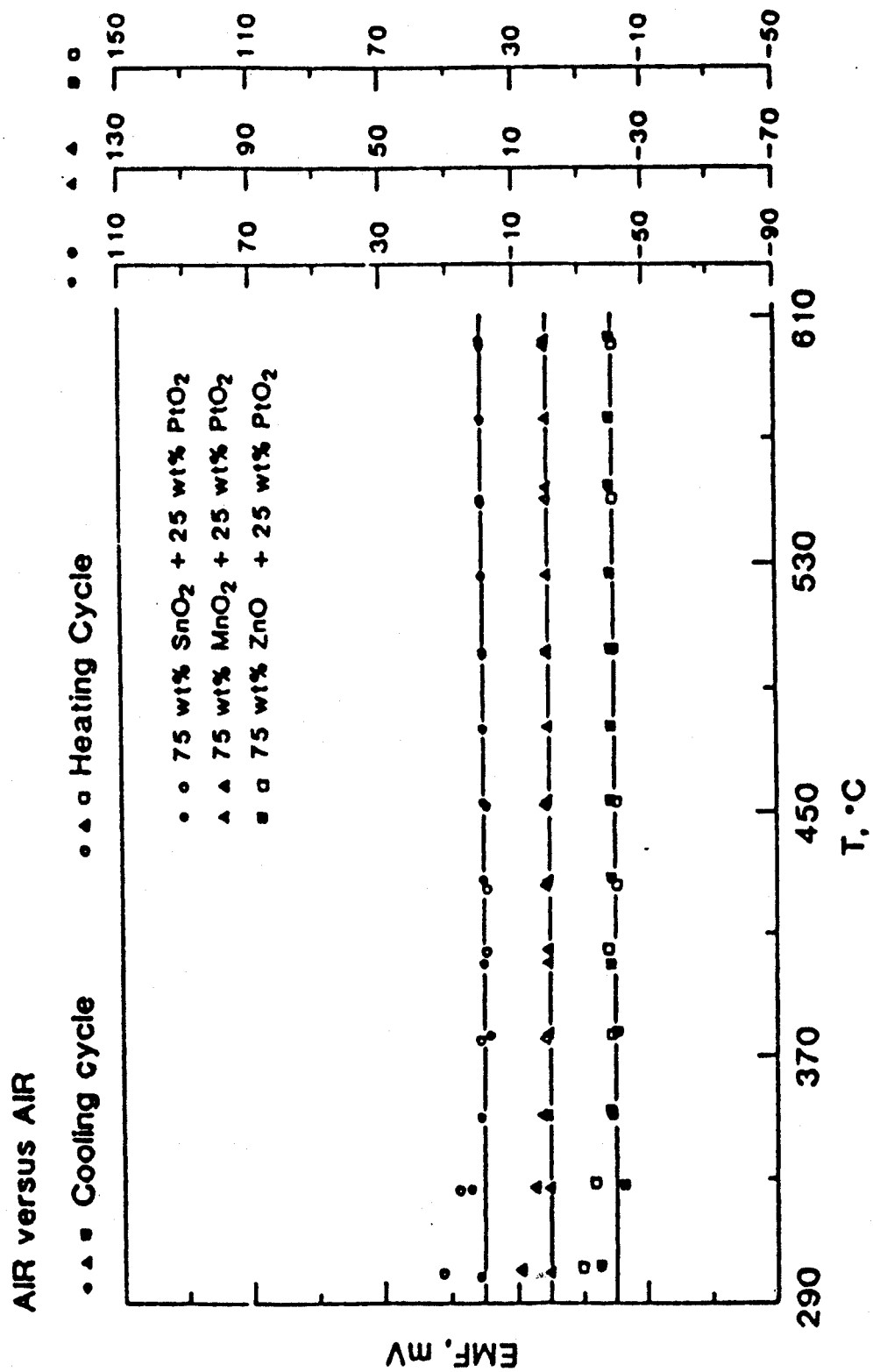
Figure 13A:
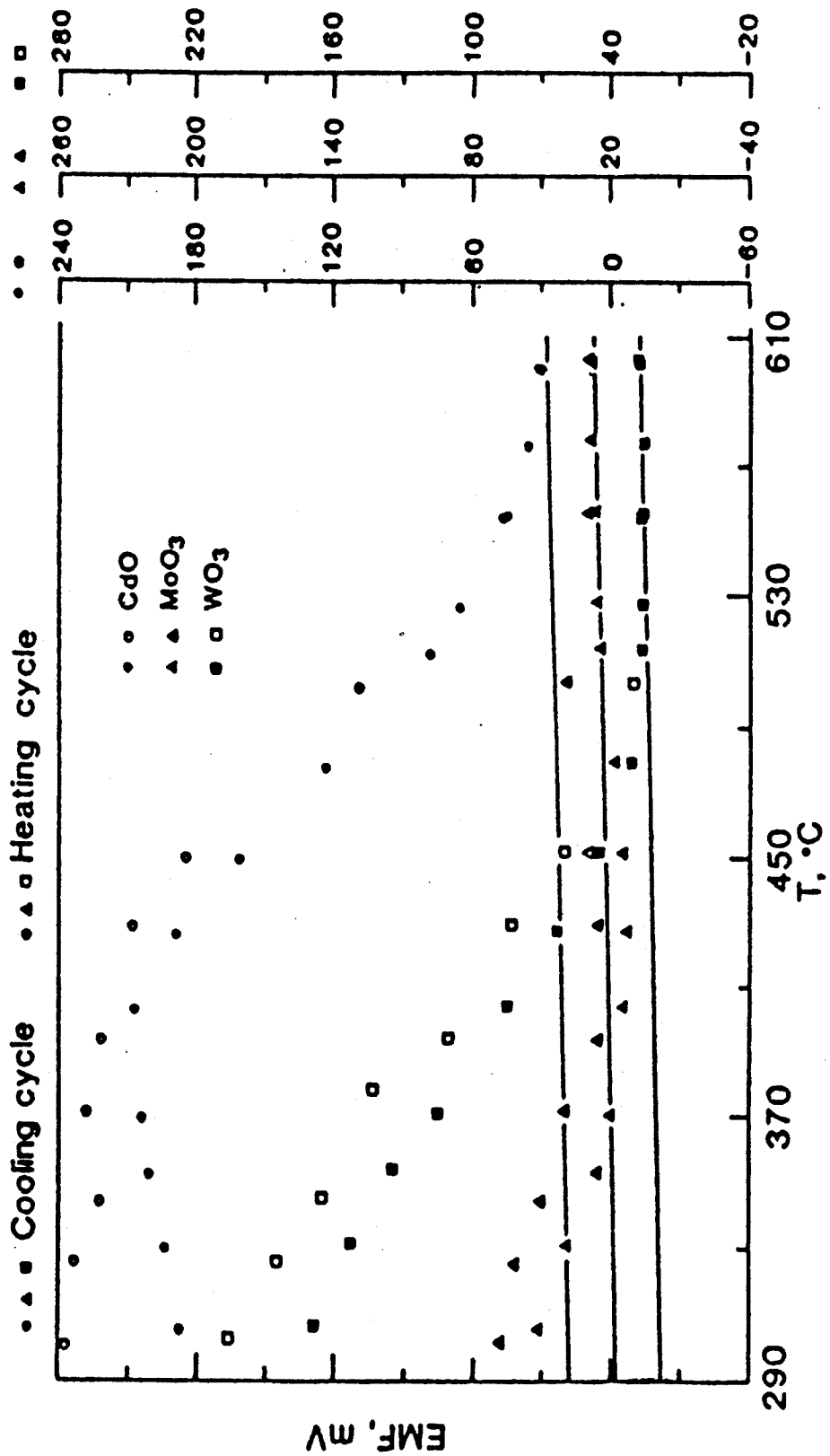
Figure 14A:
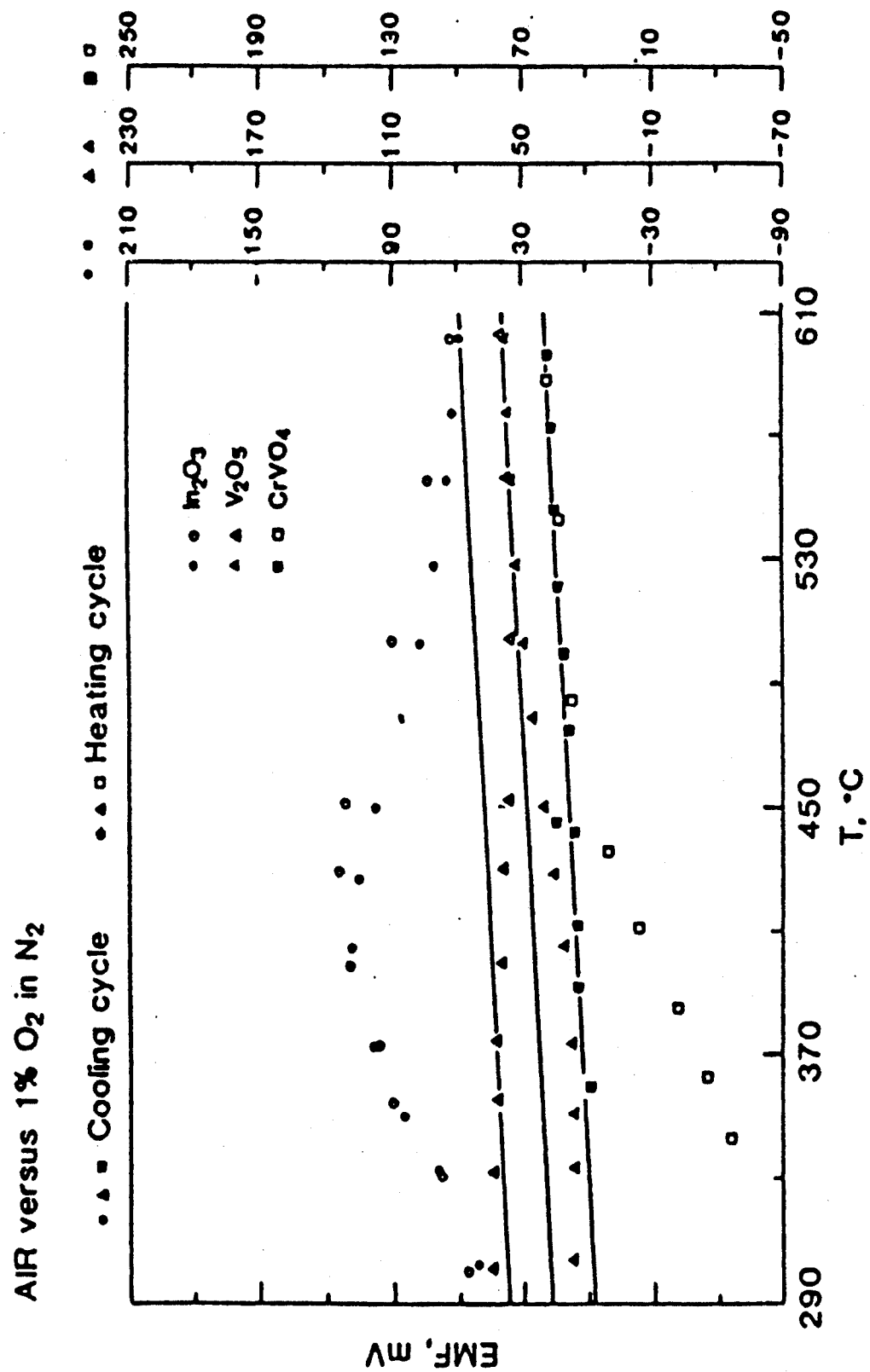
Figure 14B:
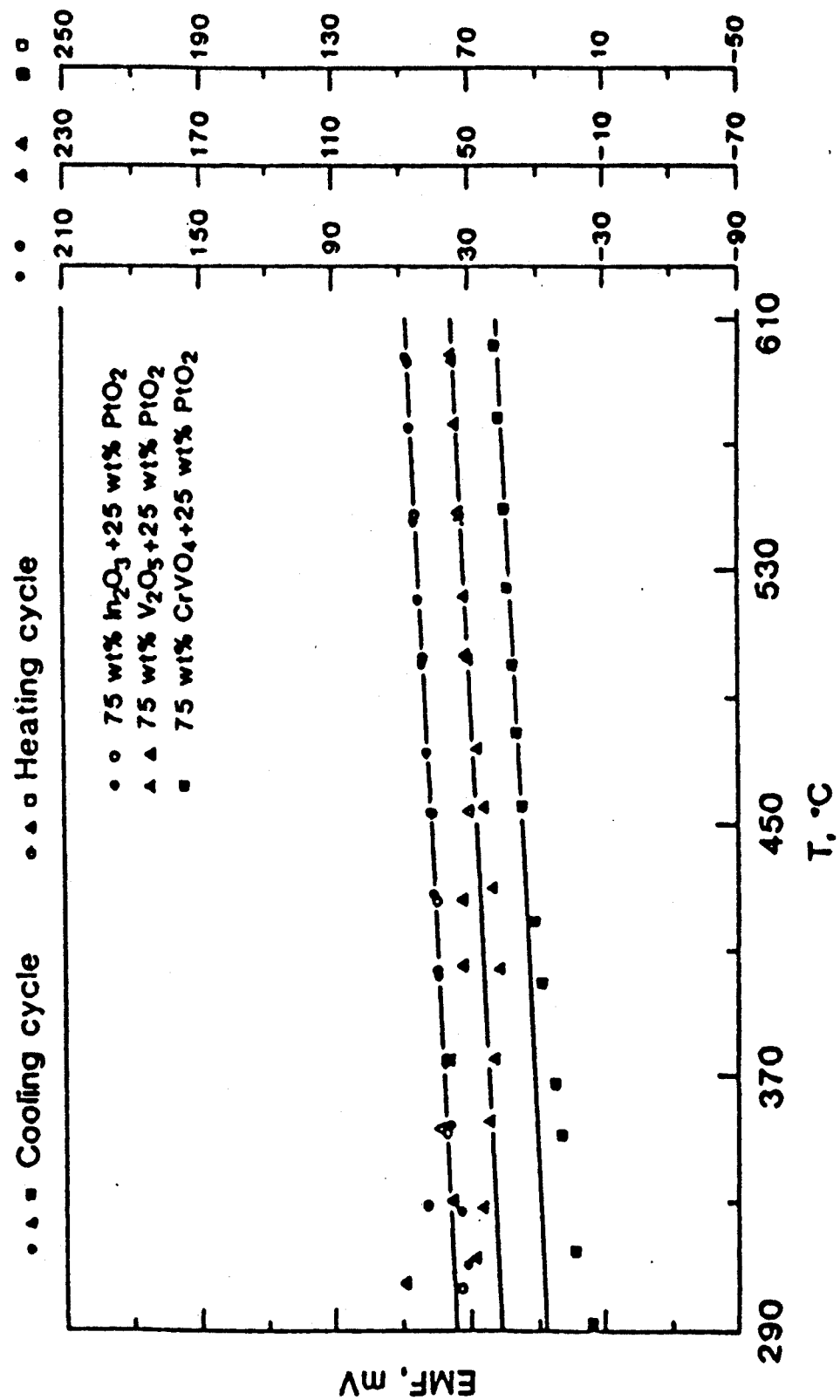
Figure 15A:
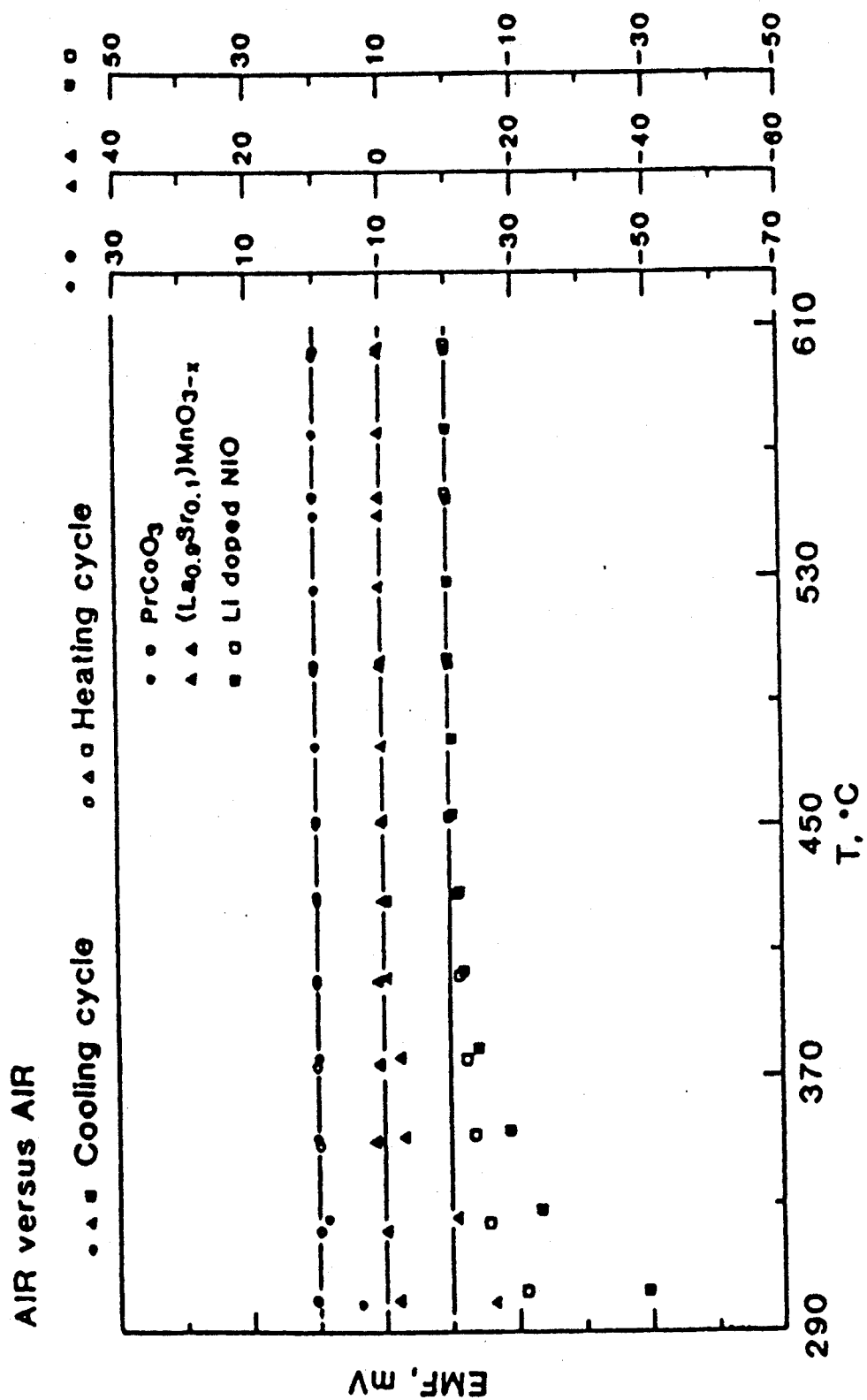
Figure 16B:
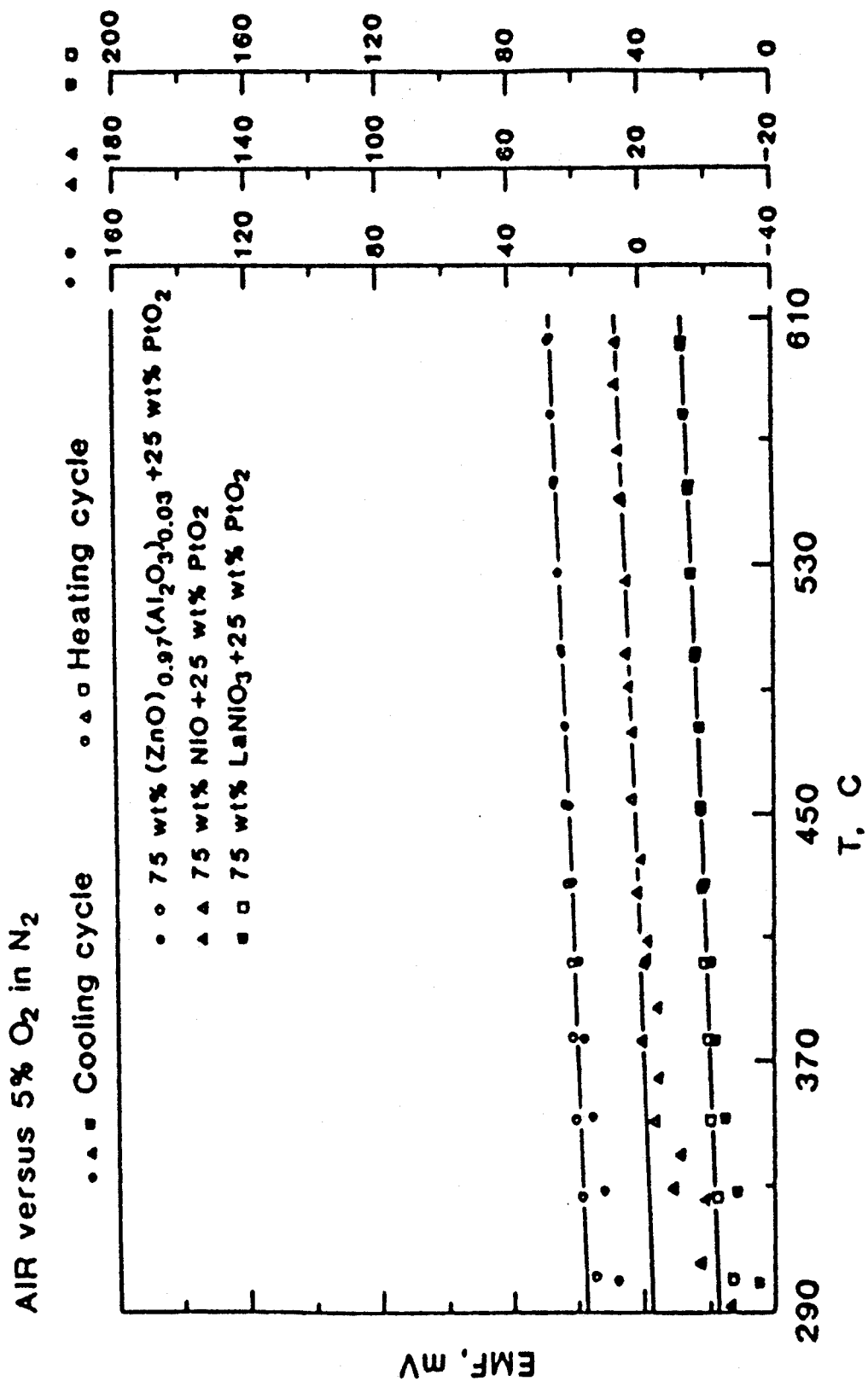
Figure 17A:
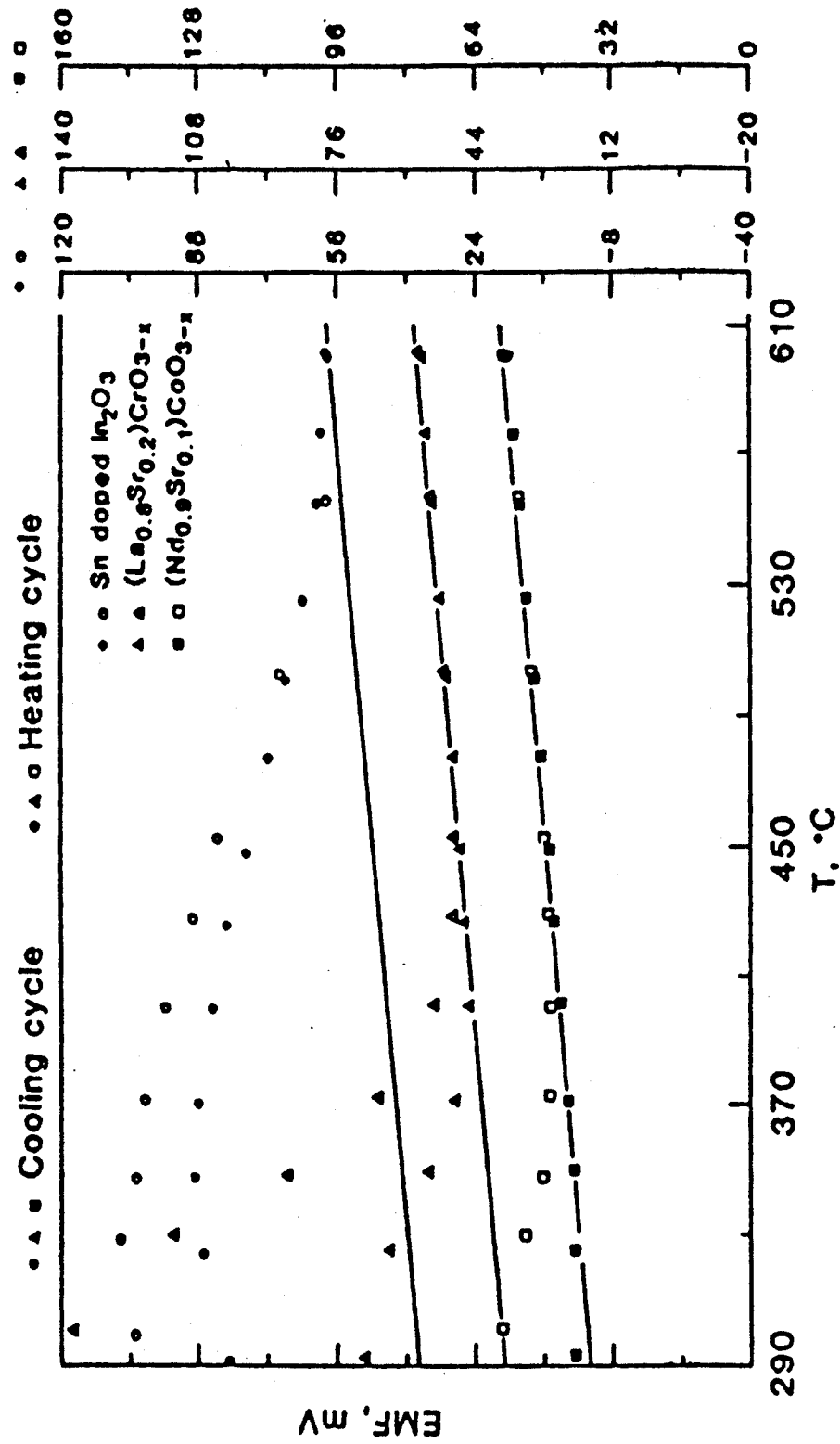
Figure 17B:
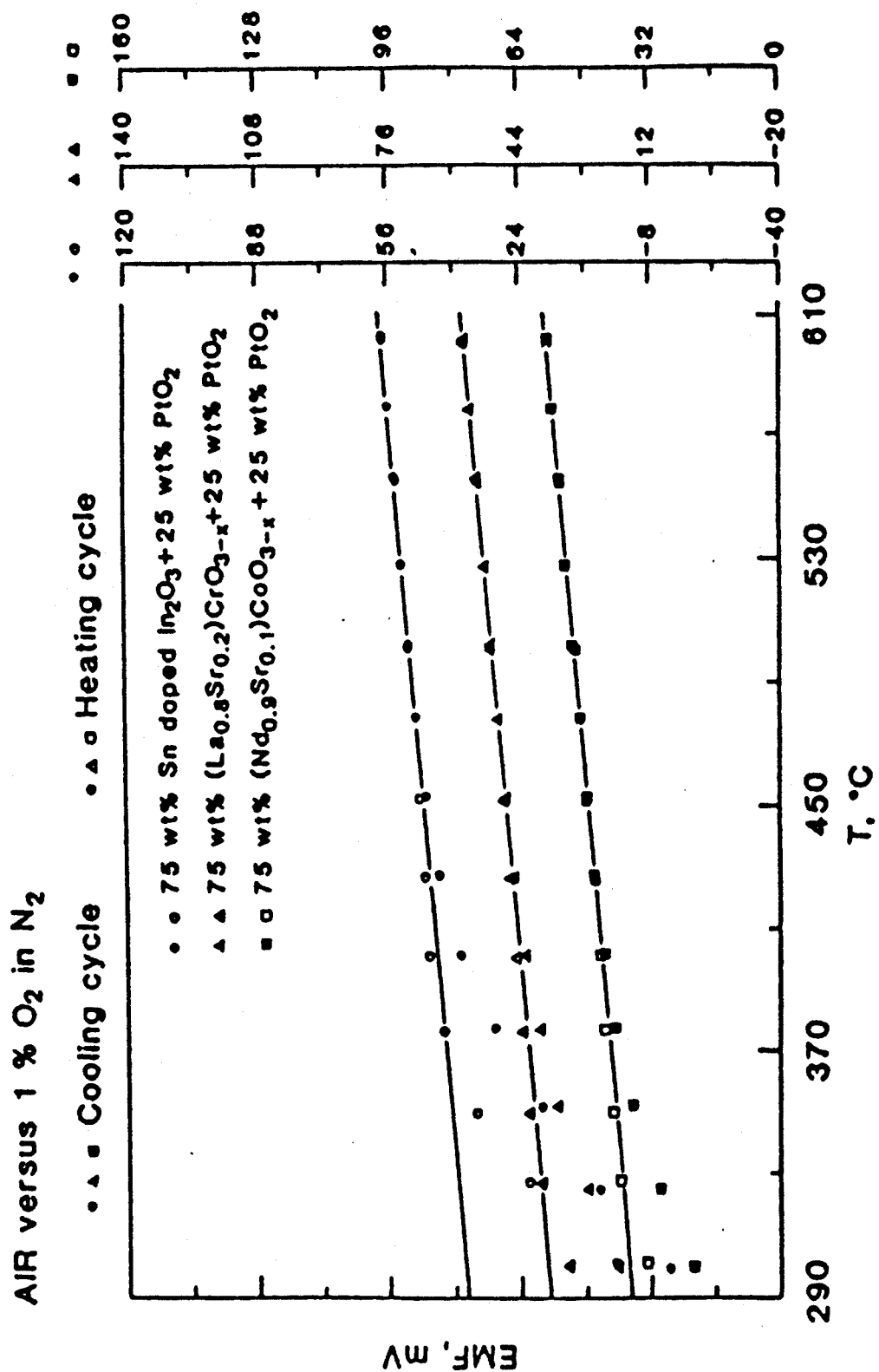
Figure 18:
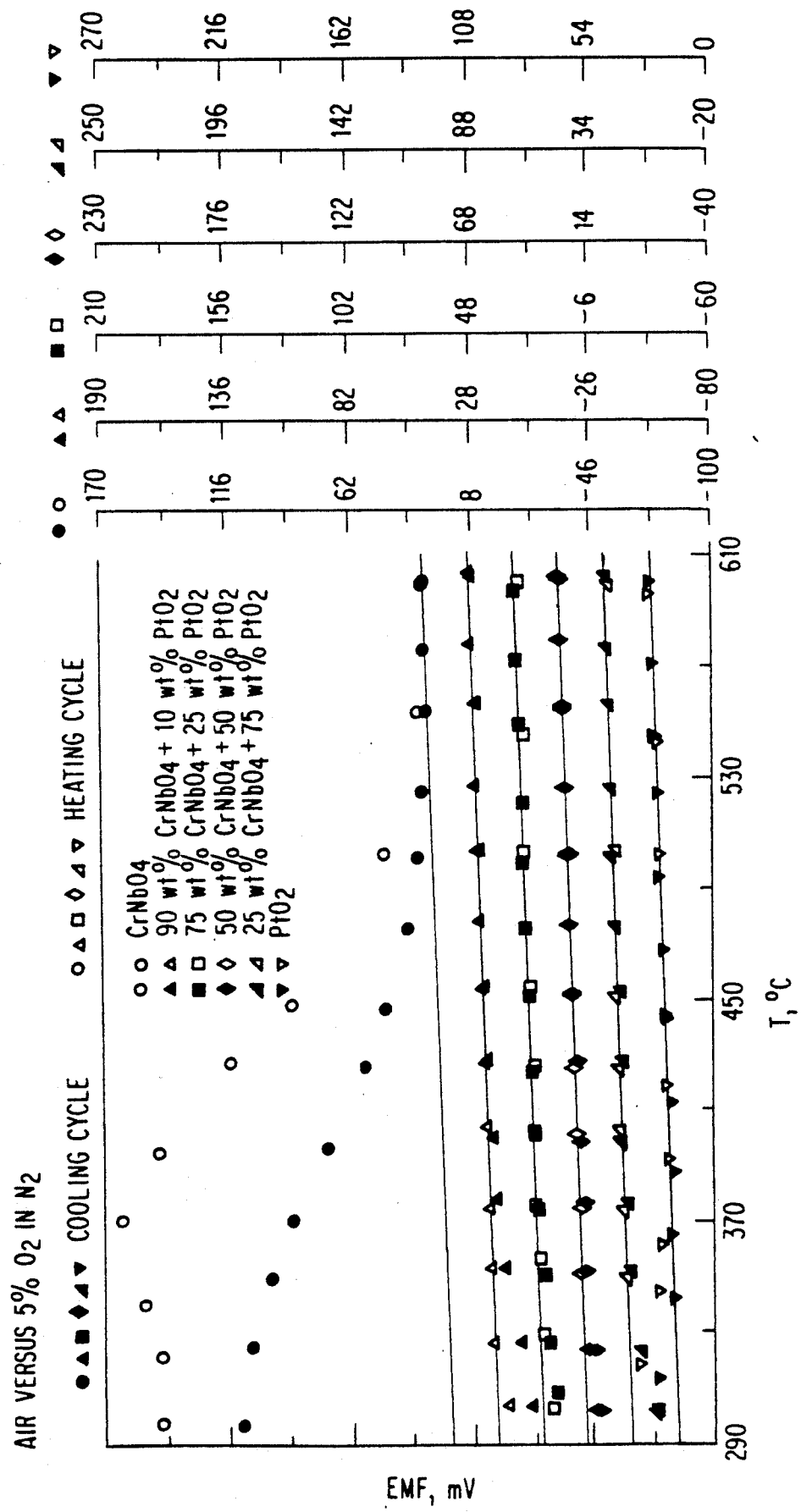
FIG. 18 is a graph comparing the individual performances of $CrNbO_4$ and $PtO_2$ electrodes with composite electrodes consisting of the two materials in various ratios.

In order to determine current voltage characteristics two cells, one provided with metal oxide only ($CrNbO_4$) and the second cell with a composite electrode consisting of 75 wt % of $CrNbO_4$ + 25 wt % $PtO_2$ were prepared by painting the respective electrode on both flat sides of sintered discs of 10 mol % yttria + 90 mol % zirconia electrolyte. The temperature of each cell was raised to 700° C. in air and the cell left to equilibrate for several hours with the surroundings before making measurements on that cell. The current voltage characteristics were recorded over several temperatures between 500° and 700° C. with a galvanostatic current interruption technique. In this method, a constant current was passed through the working electrode-electrolyte-counter electrode until a steady state voltage was reached. The current was then interrupted with a fast electronic switch (switching time <0.1 micro second), and the voltage as a function of time (10 microseconds after the current switch off) was recorded with a transient recorder. The analysis of the data for each current value gives voltage drop across the solid electrolyte (ohmic drop) and voltage drop across both electrode/electrolyte interfaces (overpotential). In FIG. 7, the overpotential-current density (current normalized to 1 $cm^2$ of the electrode/electrolyte contact area) relationship for the composite electrode is compared with the corresponding metal oxide only electrode. These results clearly show that the overpotential losses at the composite electrodes/electrolyte interface are much lower than those at the corresponding metal oxide only electrode/electrolyte interface. These experiments demonstrate the superior electrode properties of composite electrodes over their metal oxide counterparts in applications where current carrying capacities of the electrodes are important.

EXAMPLE 9

Oxygen sensors of the type shown in FIG. 1 were prepared using the electrodes described in Tables 1 to 4. In each case, the electrolyte disc used comprised a sintered mixture of alumina (50 weight percent) and 50 weight percent of a zirconia-scandia (50 weight percent) solid solution containing 4.7 mol % scandia. The sensor bodies were prepared by high temperature eutectic welding of solid electrolyte discs on to alumina tubes. Complete sensors were prepared by painting the electrode being tested (Pt, metal oxide or a composite consisting of $PtO_2$ and the metal oxide) on both flat sides of the welded electrolyte disc. The sensor assemblies were slowly heated to 600° C. to burn off the triethylene glycol and in the case of composite electrodes also to decompose $PtO_2$ to Pt.

Sensor performance tests were carried out between 300° C. and 600° C. These tests comprised (i) the determination of the cell voltage (E) with air at both electrodes and with air at the inner electrodes and oxygen-nitrogen mixtures (1 to 100 percent oxygen) at the outer electrodes; (ii) the effect on the cell voltage of varying the internal air flow rate by an order of magnitude and (iii) sensor resistance measurements with air at both the electrodes. Most tests were performed at temperature intervals of 25° C. during both a heating and a cooling cycle. In all, more than 80 sensors were tested including all the electrodes described in Tables 1-4 to show the superior characteristics of composite electrodes over its individual constituents.

Table 5 compares the resistance of sensors provided with composite electrodes with those provided with individual metal oxide only electrodes at 600° C. These values of resistances also include the electrolyte resistance which (as determined by impedance dispersion analysis of a number of cells) is around 0.6-1.2K ohm at 600° C. The resistance of sensors provided with composite electrodes is invariably much lower than those provided with semiconductor metal oxide only electrodes. Because of the much higher resistance of sensors provided with metal oxide only electrodes, they were extremely sensitive to electrical noise pick-up at temperatures below 400°-500° C. By contrast, sensors with composite electrodes showed no such sensitivity even at temperatures as low as 350° C.

TABLE 5

| | The total sensor resistance* (with air at both electrodes) at 600° C. | |
|---|---|---|
| | The total sensor resistance (k ohm) | |
| Metal Oxide | with metal oxide only electrodes | with composite electrodes consisting of 75 wt % of metal oxide + 25 wt % $PtO_2$ |
| $TbO_{2-y}$ | 5.5 | 5.1 |
| $CeO_{2-x}$ | 1918 | 73.2 |
| $Cr_2O_3$ | 63.1 | 1.02 |
| NiO | 37.9 | 4.9 |
| $Fe_2O_3$ + $Fe_3O_4$ | 238.6 | 10.1 |
| ZnO | 307 | 111 |
| $MnO_2$ | 1.7 | 1.8 |

TABLE 5-continued

The total sensor resistance* (with air at both electrodes) at 600° C.

| Metal Oxide | The total sensor resistance (k ohm) with metal oxide only electrodes | with composite electrodes consisting of 75 wt % of metal oxide + 25 wt % $PtO_2$ |
|---|---|---|
| $SnO_2$ | 439 | 46.9 |
| $WO_3$ | 155 | 1.11 |
| $MoO_3$ | 584 | 5.70 |
| CdO | 178 | 6.7 |
| $V_2O_5$ | 7.8 | 4.3 |
| $In_2O_3$ | 70.0 | 2.1 |
| $CrVO_4$ | 13.2 | 1.54 |
| $CrNbO_4$ | 214 | 0.72 |
| $(ZnO)_{0.97}(Al_2O_3)_{0.03}$ | # | 34.0 |
| Li doped NiO | 12.9 | 1.37 |
| Sn doped $In_2O_3$ | 577.7 | 2.61 |
| $LaNiO_3$ | 25.3 | 1.72 |
| $PrCoO_3$ | 5.07 | 0.91 |
| $(La_{0.8}Sr_{0.2})CrO_{3-x}$ | 15.1 | 1.33 |
| $(La_{0.9}Sr_{0.1})MnO_{3-x}$ | 8.4 | 1.32 |
| $(Nd_{0.9}Sr_{0.1})CoO_{3-x}$ | 3.57 | 1.08 |
| $(U_{0.4}Pr_{0.6})O_{2\pm x}$ | 2.9 | 2.1 |
| $(Pr_{0.7}Gd_{0.3})O_{2-x}$ | 14.2 | 3.8 |

*Electrolyte resistance at 600° C. is about 0.60–1.2 K ohm.
Resistance too high for accurate measurements.

All sensor with the oxide only or platinum electrodes gave significant zero errors (with air at both electrodes) and showed large deviations from Nernstian relationship (with air at the inner and oxygen-nitrogen mixtures at the outer electrode) at temperatures below about 450° C. In contrast, sensors provided with composite electrodes performed satisfactorily down to 350° C. or below. FIGS. 8 to 18 compare the results of several sensors provided with electrodes described in Table 1 and Table 4.

In general, the sensors with oxide only or platinum electrodes exhibited much higher sensitivity to changes in the gas flow rate than those with the metal oxide+$PtO_2$ electrodes.

These results clearly demonstrate the superior low temperature performance of the composite electrodes of the present invention over conventional metal oxide only or porous platinum electrodes on solid electrolyte oxygen sensors. In particular, the composite electrode materials enable oxygen sensors to operate reliably at temperatures as low as 300° C., well below the limit of similar sensors fitted with porous platinum or metal oxide electrodes.

EXAMPLE 10

In order to compare the response of metal oxide only and platinum electrodes to the metal oxide+$PtO_2$ electrode to sudden changes in the oxygen concentration in the gas stream, one flat side of 10 mol % $Y_2O_3$+90 mol % $ZrO_2$ sintered disc (diameter ~9.3 mm thickness 25-3.0 mm) was painted with the metal oxide only or platinum electrode and the other side with the metal oxide+$PtO_2$ electrode. Both electrodes of the cell were simultaneously exposed to a sudden change in the oxygen concentration. If both electrodes of the cell responds differently, a voltage signal is developed. The sign and shape of the voltage-time curve provide information on the relative speed of response of both electrodes. These measurements were made on several couples at temperatures between 300° C. and 500° C. to show the superior characteristics of composite electrodes over their metal oxide only or Pt counterparts. In all cases, the composite electrode consisting of a metal oxide+$PtO_2$ responded much faster compared to the metal oxide only or porous platinum electrode.

These measurements demonstrate quite clearly that composite electrode have much faster rates for oxygen exchange reaction compared the metal oxide only or platinum electrodes.

What is claimed is:

1. An oxygen ion-conducting solid electrolyte device characterized in that the solid electrolyte is impervious to gas and is selected from the group consisting of zirconia, hafnia, thoria, and ceria, doped or alloyed with one or more oxides selected from the group comprising calcia, magnesia, yttria, scandia and rare earth oxides, said solid electrolyte carrying at least one electrode which comprises a mixture of a minor proportion of a noble metal selected from the group consisting of platinum, silver, gold, palladium, iridium or rhodium and mixtures or alloys of any two or more of said metals, and a major proportion of a semiconducting metal oxide with either electronic n-type or hole p-type conductivity selected from the semiconducting oxides or complex oxides of one or more of the transition metals having atomic numbers 24–30, metals having atomic numbers 49–50 and the lanthanides having atomic numbers 57–71 wherein said noble metal is present in an amount from an amount effective to lower the time constant and the electrode resistance of said electrode as compared to either of said noble metal alone or said semiconducting metal oxide alone upto an amount of 40% by weight.

2. A device as claimed in claim 1, characterized in that the noble metal is present in the electrode in an amount of 15-40% by weight.

3. A device as claimed in claim 1, characterized in that the semiconductor oxide component is a compound or a solid solution between one or more of simple binary metal oxides.

4. A device as claimed in claim 1, characterized in that the semiconductor oxide component is a mixture of one or more simple metal oxides, compounds or solid solutions.

5. A device as claimed in claim 1, characterized in that the semiconductor oxide component also contains other than essential ingredients, one or more of an insulator, ionic conductor or other semiconductor phases.

6. A device as claimed in claim 1, characterized in that the electrode material is formed as a surface layer on the body of the solid electrolyte.

7. A device as claimed in claim 6, characterized in that the surface layer is formed as a thin region on and extending beneath the surface of the solid electrolyte, the said region being enriched in the electrode material.

8. An oxygen ion-conducting solid electrolyte device, characterized in that the solid electrolyte is impervious to gas and is selected from the group comprising zirconia, thoria or ceria, doped or alloyed with one or more oxides selected from the group consisting of calcia, magnesia, yttria, scandia and rare earth oxides, said solid electrolyte carrying at least one electrode which comprises a mixture of a minor proportion of a noble metal selected from the group consisting of platinum, silver, gold or palladium, and mixtures or alloys of any two or more of said metals and a major proportion of a semi-conducting metal oxide with electronic n-type conductivity selected from the semiconducting oxides or complex oxides of one or more of the transition metals having atomic numbers 24–30, metals having atomic numbers 49–50 and the lanthanides having atomic numbers 57–71 wherein said noble metal is present in an amount from an amount effective to lower the time constant and the electrode resistance of said electrode as compared to either of said noble metal alone or said semiconducting metal oxide alone upto an amount of 40% by weight.

9. A device as claimed in claim 8, characterized in that the noble metal is present in the electrode in a proportion of 15-40% by weight.

10. A device as claimed in claim 8, characterized in that the semiconductor oxide component is a compound or solid solution between one or more simple binary metal oxides.

11. A device as claimed in claim 8, characterized in that the semiconductor oxide component is a mixture of one or more simple metal oxides, compounds or solid solutions.

12. A device as claimed in claim 8, characterized in that the semiconductor oxide component also contains one or more of an insulator, ionic conductor or other semiconductor phases.

13. A device as claimed in claim 8, characterized in that the electrode material is formed as a surface layer on the body of the solid electrolyte.

14. A device as claimed in claim 13, characterized in that the surface layer is formed as a thin porous coating of a mixture of noble metals and the semiconducting metal oxide.

15. A device as claimed in claim 13, characterized in that the surface layer is formed as a thin region on and extending beneath the surface of the solid electrolyte, the said region being enriched in the electrode materials.

* * * * *